US012685452B2

(12) United States Patent
Siddique et al.

(10) Patent No.: US 12,685,452 B2
(45) Date of Patent: Jul. 21, 2026

(54) METHODS AND SYSTEMS FOR POLARIZED PHOTOPLETHYSMOGRAPHY (PPG) AND BIOSIGNAL ANALYSIS

(71) Applicant: Samsung Electronics Co., Ltd., Gyeonggi-do (KR)

(72) Inventors: Radwanul Hasan Siddique, Monrovia, CA (US); Shailabh Kumar, Pasadena, CA (US)

(73) Assignee: Samsung Electronics Co., Ltd. (KR)

( * ) Notice: Subject to any disclaimer, the term of this patent is extended or adjusted under 35 U.S.C. 154(b) by 99 days.

(21) Appl. No.: 18/103,855

(22) Filed: Jan. 31, 2023

(65) Prior Publication Data

US 2024/0065567 A1 Feb. 29, 2024

Related U.S. Application Data

(60) Provisional application No. 63/421,710, filed on Nov. 2, 2022, provisional application No. 63/400,213, filed on Aug. 23, 2022.

(51) Int. Cl.
*A61B 5/024* (2006.01)
(52) U.S. Cl.
CPC .. *A61B 5/02427* (2013.01); *A61B 2562/0233* (2013.01)
(58) Field of Classification Search
CPC ............ A61B 5/02427; A61B 5/14552; A61B 5/02141; A61B 5/0075; A61B 5/0205;
(Continued)

(56) References Cited

U.S. PATENT DOCUMENTS 6,070,093 A * 5/2000 Oosta ................... A61B 5/1455
600/316
8,768,424 B2 7/2014 Crowe et al.
(Continued)

FOREIGN PATENT DOCUMENTS

CN 114786577 7/2022
EP 3 766 403 1/2021
(Continued)

OTHER PUBLICATIONS

Lee et al., research article "Stretchable PPG sensor with light polarization for physical activity-permissible monitoring" Scie. Adv. 8, eabm3622, Apr. 13, 2022 8 pages (Year: 2022).*
(Continued)

*Primary Examiner* — Boniface N Nganga
(74) *Attorney, Agent, or Firm* — The Farrell Law Firm, P.C.

(57) ABSTRACT

The disclosure is directed to a system and a method for biosignal detection, the method including emitting an electromagnetic spectral emission, including polarized light, that is reflected on a surface, collecting attributes from the reflected electromagnetic spectral emission, calculating Stokes parameters based on the collected attributes, determining at least one signal based on the Stokes parameters, and analyzing the at least one signal to estimate health-related information, wherein the collected attributes comprise at least one of a light intensity of a predetermined polarization state, a light intensity for a wavelength range, and a light intensity for multiple pixels.

19 Claims, 14 Drawing Sheets

(58) Field of Classification Search

CPC .......... A61B 5/7275; A61B 2562/0233; A61B
2562/046

See application file for complete search history.

(56) References Cited

U.S. PATENT DOCUMENTS

| | | | |
|---|---|---|---|
| 9,513,162 | B2 | 12/2016 | Herrick et al. |
| 10,271,746 | B2 | 4/2019 | Jeanne et al. |
| 11,054,304 | B2 | 7/2021 | Ozawa |
| 11,103,150 | B2 | 8/2021 | Crowe et al. |
| 11,405,601 | B2 | 8/2022 | McEldowney |
| 2015/0018645 | A1 | 1/2015 | Farkas et al. |
| 2018/0325397 | A1 | 11/2018 | Presura et al. |
| 2019/0167118 | A1 | 6/2019 | Vilenskil et al. |
| 2021/0059585 | A1 | 3/2021 | Choi et al. |
| 2021/0148811 | A1 | 5/2021 | Shaw et al. |
| 2021/0190593 | A1* | 6/2021 | Yao ...................... G02B 5/3025 |
| 2021/0191021 | A1 | 6/2021 | Siddique et al. |
| 2021/0201496 | A1 | 7/2021 | De Haan et al. |
| 2021/0219884 | A1 | 7/2021 | De Haan |
| 2021/0311240 | A1 | 10/2021 | Siddique et al. |
| 2021/0333150 | A1 | 10/2021 | McEldowney et al. |
| 2021/0386308 | A1 | 12/2021 | Ben Ishay et al. |
| 2022/0007952 | A1 | 1/2022 | Lee et al. |
| 2022/0047221 | A1 | 2/2022 | De Haan |

FOREIGN PATENT DOCUMENTS

| | | | | |
|---|---|---|---|---|
| EP | | 4 384 801 | 6/2024 | |
| TW | | I689752 | 4/2020 | |
| WO | WO 2022/064273 | | 3/2022 | |
| WO | WO 2023/018846 | | 2/2023 | |
| WO | WO-2023018846 A1 * | | 2/2023 | ........... A61B 5/1455 |
| WO | WO-2023105242 A1 * | | 6/2023 | ......... A61B 1/00004 |

OTHER PUBLICATIONS

European Search Report dated Dec. 14, 2023 issued in counterpart application No. 23188022.0-1113, 7 pages.

Asare, L. et al., "Multi-spectral photoplethysmography biosensor", Proc. of SPIE, (vol. 8073) Optical Sensors 2011; and Photonic Crystal Fibers V, 80731Z, May 9, 2011, pp. 6.

Vavrinsky et al., "The Current State of Optical Sensors in Medical Wearables", Biosensors 2022 (vol. 12, Issue 4, No. 217), Apr. 6, 2022, pp. 40.

Lee, Gae Hwang et al., "Stretchable PPG sensor with light polarization for physical activity-permissible monitoring", Sci. Adv. 8, eabm3622 (2022) Apr. 13, 2022, pp. 9.

Chakraborty, Supriya et al., "PSPPG: Polarization Sensitive Photoplethysmography", Procedia Engineering 168 (2016) 1275-1278.

EP Communication Report dated Jun. 24, 2025 issued in counterpart application No. 23188022.0-1113, 7 pages.

EP Communication Report dated Mar. 31, 2026 issued in counterpart application No. 23188022.0-1113, 9 pages.

* cited by examiner

Light Source
500a

Detector
500b

Pattern 1

Pattern 2

Pattern 3

Pattern 4

METHODS AND SYSTEMS FOR POLARIZED PHOTOPLETHYSMOGRAPHY (PPG) AND BIOSIGNAL ANALYSIS

PRIORITY

This application is based on and claims priority under 35 U.S.C. § 119(e) to U.S. Provisional Patent Application Ser. No. 63/400,213, filed on Aug. 23, 2022, and Provisional Patent Application 63/421,710, filed on Nov. 2, 2022, the entire contents of which are incorporated herein by reference.

TECHNICAL AREA

The present disclosure relates generally to systems and methods for biosignal detection and analysis using photoplethysmography (PPG) sensors.

BACKGROUND

Optical sensors play an increasingly important role in the development of medical diagnostic device, and they can be widely used to measure the physiology of the human body.

Research on skin-attachable electronic devices including optical devices (e.g., wearable devices) for obtaining health-information is in progress. Such skin-attachable devices include biosensors for obtaining bio-information. For example, a PPG sensor may obtain a PPG signal from a user, and by analyzing the PPG signal, vital signs such as a user's blood pressure, arrhythmia, heart rate, and/or oxygen saturation may be obtained.

Moreover, on chip polarizing filters in light sources and detectors can be used to remove the direct reflection component and make the measurement of healthcare signatures through wearable devices more accurate with on-chip polarization sensor/photo diode (PD) by studying different features of polarization information (e.g., angle of polarization (AoP), degree of polarization (DoP), angle of linear polarization (AoLP), degree of linear polarization (DoLP), angle of circular polarization (AoCP), degree of circular polarization (DoCP)) with respect to different spectrums. For example, the polarization information can be used to improve the accuracy of vital signs monitoring while a user is in motion. In addition, signatures for different biomolecules or health characteristics may be obtained by studying the different features of polarization information. Thus, improvements to systems and methods for obtaining bio-information using optical biosensors based on polarization characteristics are highly desirable.

SUMMARY

The present disclosure has been made to address at least the disadvantages described above and to provide at least the advantages described below.

According to an aspect of the disclosure, a method for biosignal detection and analysis is provided. The method includes emitting an electromagnetic spectral emission, including polarized light, that is reflected on a surface, collecting attributes from the reflected electromagnetic spectral emission, calculating Stokes parameters based on the collected attributes, determining at least one signal based on the Stokes parameters, and analyzing the at least one signal to estimate health-related information, wherein the collected attributes comprise at least one of a light intensity of a predetermined polarization state, a light intensity for a wavelength range, and a light intensity for multiple pixels.

According to another aspect of the disclosure, a system for bio signal detection and analysis is provided. The system includes a light source configured to emit an electromagnetic spectral emission, including polarized light, reflected on a surface, a detector configured to collect attributes of the reflected electromagnetic spectral emission, and a processor. The processor is configured to calculate Stokes parameters based on the collected attributes, determine at least one signal based on the Stokes parameters, and analyze the at least one signal to estimate health-related information, wherein the collected attributes comprise at least one of a light intensity of a predetermined polarization state, a light intensity for a wavelength range, and a light intensity for multiple pixels.

According to another aspect of the disclosure, a method for bio signal detection and analysis is provided. The method includes emitting polarized light that is reflected on a surface, detecting the reflected polarized light using a pixel having four polarizing filters, calculating Stokes parameters based on attributes of the polarized light identified using the four polarizing filters, determining at least one signal based on the Stokes parameters, and analyzing the at least one signal to estimate health-related information, wherein the attributes comprise at least one of a light intensity of a predetermined polarization state, a light intensity for a wavelength range, and a light intensity for multiple pixels

BRIEF DESCRIPTION OF THE DRAWINGS

The above and other aspects, features, and advantages of certain embodiments of the present disclosure will be more apparent from the following detailed description, taken in conjunction with the accompanying drawings, in which.

DETAILED DESCRIPTION

Figure 1A:
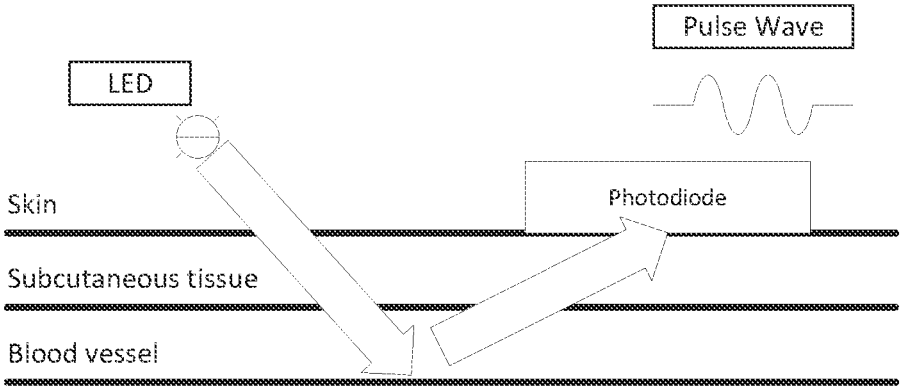
FIG. 1A illustrates a PPG sensor system, according to an embodiment.

Hereinafter, embodiments of the present disclosure are described in detail with reference to the accompanying drawings. It should be noted that the same elements will be designated by the same reference numerals although they are shown in different drawings. In the following description, specific details such as detailed configurations and components are merely provided to assist with the overall understanding of the embodiments of the present disclosure. Therefore, it should be apparent to those skilled in the art that various changes and modifications of the embodiments described herein may be made without departing from the scope of the present disclosure. In addition, descriptions of well-known functions and constructions are omitted for clarity and conciseness. The terms described below are terms defined in consideration of the functions in the present disclosure, and may be different according to users, intentions of the users, or customs. Therefore, the definitions of the terms should be determined based on the contents throughout this specification.

The present disclosure may have various modifications and various embodiments, among which embodiments are described below in detail with reference to the accompanying drawings. However, it should be understood that the present disclosure is not limited to the embodiments, but includes all modifications, equivalents, and alternatives within the scope of the present disclosure.

Although the terms including an ordinal number such as first, second, etc. may be used for describing various elements, the structural elements are not restricted by the terms. The terms are used to distinguish one element from another element. For example, without departing from the scope of the present disclosure, a first structural element may be referred to as a second structural element. Similarly, the second structural element may also be referred to as the first structural element. As used herein, the term "and/or" includes any and all combinations of one or more associated items.

The terms used herein are merely used to describe various embodiments of the present disclosure but are not intended to limit the present disclosure. Singular forms are intended to include plural forms unless the context clearly indicates otherwise. In the present disclosure, it should be understood that the terms "include" or "have" indicate existence of a feature, a number, a step, an operation, a structural element, parts, or a combination thereof, and do not exclude the existence or probability of the addition of one or more other features, numerals, steps, operations, structural elements, parts, or combinations thereof.

Unless defined differently, all terms used herein have the same meanings as those understood by a person skilled in the art to which the present disclosure belongs. Terms such as those defined in a generally used dictionary are to be interpreted to have the same meanings as the contextual meanings in the relevant field of art, and are not to be interpreted to have ideal or excessively formal meanings unless clearly defined in the present disclosure.

The electronic device according to one embodiment may be one of various types of electronic devices utilizing sensors and/or storage devices. The electronic devices may include, for example, a portable communication device (e.g., a smart phone), a computer, a portable multimedia device, a portable medical device, a camera, a wearable device, or a home appliance. According to one embodiment of the disclosure, an electronic device is not limited to those described above.

The terms used in the present disclosure are not intended to limit the present disclosure but are intended to include various changes, equivalents, or replacements for a corresponding embodiment. With regard to the descriptions of the accompanying drawings, similar reference numerals may be used to refer to similar or related elements.

A singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, terms such as "$1^{st}$," "$2^{nd}$," "first," and "second" may be used to distinguish a corresponding component from another component, but are not intended to limit the components in other aspects (e.g., importance or order). It is intended that if an element (e.g., a first element) is referred to, with or without the term "operatively" or "communicatively", as "coupled with," "coupled to," "connected with," or "connected to" another element (e.g., a second element), it indicates that the element may be coupled with the other element directly (e.g., wired), wirelessly, or via a third element.

As used herein, the term "module" may include a unit implemented in hardware, software, firmware, or combination thereof, and may interchangeably be used with other terms, for example, "logic," "logic block," "part," and "circuitry." A module may be a single integral component, or a minimum unit or part thereof, adapted to perform one or more functions. For example, according to one embodiment, a module may be implemented in a form of an application-specific integrated circuit (ASIC).

In this disclosure, a light (e.g., electromagnetic spectral emission) detection position can be at different locations (e.g., spatially varying, tilted, etc.). In addition, a light source can have collimator elements, diffractive optical elements, etc.

Furthermore, multiple methods of light detection and analysis are described herein. For example, different types of polarized and non-polarized light may be emitted and analyzed to provide biosignals for reducing an SNR and improve detection of bodily parameters.

According to an embodiment, the present disclosure provides a method including the steps of emitting light (e.g., polarized light), collecting the light, collecting attributes from the collected light (e.g., attributes regarding a lighting intensity at a certain polarization states and a wavelength in a range, and for multiple pixels (multispectral)), calculating Stokes parameters, calculating signals based on the Stokes parameters, repeating some or all of the abovementioned steps, and analyzing the data.

The emitted light can be one or more of collimated light, diffused light, polarized light, multispectral light, pulsed light, continuous light, in the visible or infrared spectrum.

Collecting the light may be performed on at least one pixel.

The attributes from the collected light can be one or more of a spectrum, a polarization state, a light intensity, and a depth (e.g., a time of flight).

At least one pixel can detect both a wavelength range (e.g., 0.5 nanometers (nm) to 400 nm) and one polarization state, and can have hardware filters (nanostructures or others) for allowing the wavelength range and polarization state to pass through.

Calculating the Stokes parameters may be done for at least one pixel using intensity data from the pixel that had a polarization state and wavelength range filter.

The signals calculated may include at least one of a depolarization state (e.g., a degree of polarization changed from an initial to a final state), retardance (e.g., an angle of polarization), diattenuation (e.g., a reduction in intensity), spectral changes, and a depth estimation.

The method can be used for gathering information related to biosignal detection. This information may include, and is not limited to, a heart rate (HR), a respiratory rate, hypertension signatures, a red blood cell concentration, a blood saturation level, continuous blood pressure, a pulse rate, a pulse pressure, cardiovascular conditions, stroke volume, a cardiac output, a one lead electrocardiogram (ECG), a systematic vascular resistance, a cardiac index, a mean arterial pressure, antioxidants, melanoma, triglyceride, cholesterol, and/or beta carotene.

Accordingly, the present disclosure provides methods and systems for a polarization controlled light source and multispectral full-Stokes (linear and circular) polarization PPG sensors.

The present disclosure may modulate the phase and polarization of the light simultaneously to improve the signal-to-background ratio (SBR) and angle-dependent properties.

Polarization and multispectral information may be obtained for detecting polarization and spectral sensitive physiological parameters and molecular information of antioxidants, melanoma, triglyceride, and cholesterol.

The present disclosure advantageously provides an on-chip design with high efficiency with detection of all polarization states, focusing light using the filters with reduced angle-dependency and a high field of view (FOV). In addition, the present disclosure may reduce signal to background noise and detect polarization sensitive targets/molecules.

Accordingly, methods and systems for biosensing using a PPG sensor system, analysis, and feedback ecosystem are provided. A polarization controlled light source (a light emitting device (LED), a laser diode, or a vertical-cavity surface-emitting laser (VCSEL)) with passive or active polarization filters (nanostructured and/or liquid crystals) may be provided. Additionally, a compact PPG sensor system may be provided that utilizes complete on-chip polarization, and multispectral sensors (PD, avalanche photodiode (APD), and single-photon avalanche photodiode (SPAD)). Additionally, a suite of detection and analysis algorithms that utilize the multiple sensors may be provided. Further, an integrated feedback loop system that includes measuring the body's physiological parameter response to polarized light is provided.

A method and system of using polarization-controlled light source and multispectral full-Stokes polarization PPG sensors may be provided. The system may modulate the phase and polarization of the light simultaneously to improve SBR and angle-dependent field of view (FOV) properties.

Polarization and multispectral information for detecting polarization and spectral sensitive physiological parameters and molecular information of antioxidants, melanoma, triglyceride, and cholesterol may also be provided.

Accordingly, a highly efficient on-chip design, for all detectable polarization states focusing light using the filters, reduced angle-dependency and high FOV, reduced signal to background noise, and detecting polarization sensitive targets/molecules may be provided.

A PPG sensor system uses a non-contact non-invasive optical imaging technique which uses intensity and color-based information of transmitted or reflected light to measure physiological parameters. For example, a PPG sensor system may record a reflected/transmitted time-varying signal. Temporal analysis of spectrum and intensity information of the transmitted or reflected light may include important health-related information. In addition, PPG may be used for blood pulsation and HR measurements, utilized to obtain cardiovascular and respiratory information.

FIG. 1A illustrates a PPG sensor system, according to an embodiment.

As illustrated in FIG. 1A, a light emitting diode (LED) may emit light towards the skin of the user through the subcutaneous tissue, and may be reflected off of the blood vessel. The reflected light may be received by a PD and include a particular pulse wave or other bioinformation. Characteristics of the pulse wave may reveal several different types of physiological information (or patterns) about the user (e.g., blood pulsation and HR measurements, cardiovascular and respiratory information, etc.).

Light reflected from the patient's skin and captured by the PPG sensor system may include three components:

1. Light that is a direct reflection from the skin surface. This type of light may have a reduced signal to noise ratio (SNR).
2. Light that is a reflection from superficial layer of tissues, scattering through the epidermis cuticles. This type of light may impede or interfere with important/relevant biosignals.
3. Backscattered light from deep layer Dermis tissues. This type of light may be weak to capture, and may include hard to classify signals among different molecules in the layer.

Optical measurements with PPG sensors of skin microcirculation (e.g., blood volume and flow) may provide continuous readout information of critical parameters including heartrate and oxygen saturation (O2 saturation), and may indicate health conditions including hypertension, cardiovascular ailments, and anemia if, for example, a higher and improved SBR is made possible with deeper penetration of light through skin.

In addition, wearable PPG sensors may face various foundational challenges such as optical noise (e.g., scattering/reflection and no collimation); challenges arising based on the sensor location on the body (e.g., wrist versus ear versus arm); skin tone (e.g., some skin tones provide less signal absorption and less penetration); the crossover problem (e.g., artifacts cause by motion/activity); and low perfusion (e.g., issues related to obesity, diabetes, heart conditions, and arterial diseases each lowering blood perfusion).

Accordingly, measurements may be difficult and inaccurate due to interfering signals, such as direct reflection from the skin surface or tissues, backscattered light from deep dermal tissues, and/or motion-related artifacts.

A method and system for using a compact PPG sensor system that utilizes on-chip polarization characteristics and on-chip multispectral sensor characteristics may be provided. "On-chip" may mean that components that are described as "on-chip" are directly included as a part of the chip. That is, on-chip polarizing filters for both a light source and a light sensor may be used, which can be readily fabricated, scaled, and incorporated monolithically in wearable devices, thereby improving the accuracy of measurements by removing (or reducing) the effects of direct reflection and scattering, and removing (or reducing) motion-artifact related noise).

Polarization sensors combined with signal processing can help isolate/reveal signal(s) from different biological components, such as blood, skin antioxidants, fat tissue, and more. These improvements can be used to predict ailments, such as hypertension, cardiovascular ailments, anemia and more.

The PPG sensor system may include a polarization controlled light source (e.g., an LED, laser diode or VCSELL) with passive or active polarization optics (e.g., nanostructures or liquid crystals). The polarization optics may be static (where a polarization state is predetermined by the filter or dynamic (where a polarization state can be changed by the filter). The method and system may simultaneously provide an emission using a polarization controlled light source and detect a multispectral full-Stokes polarization using PPG sensors. Accordingly, the method and system may simultaneously measure multiple polarization states emitted by an electromagnetic spectral emission source (e.g., the polarization controlled light source).

The method and system may use a detector to detect multiple states of polarization. A polarization state may refer to a polarization type or polarization angle of an electromagnetic spectral emission. For example, a polarization state may be linear polarization, circular polarization, or elliptical polarization.

Figure 1B:
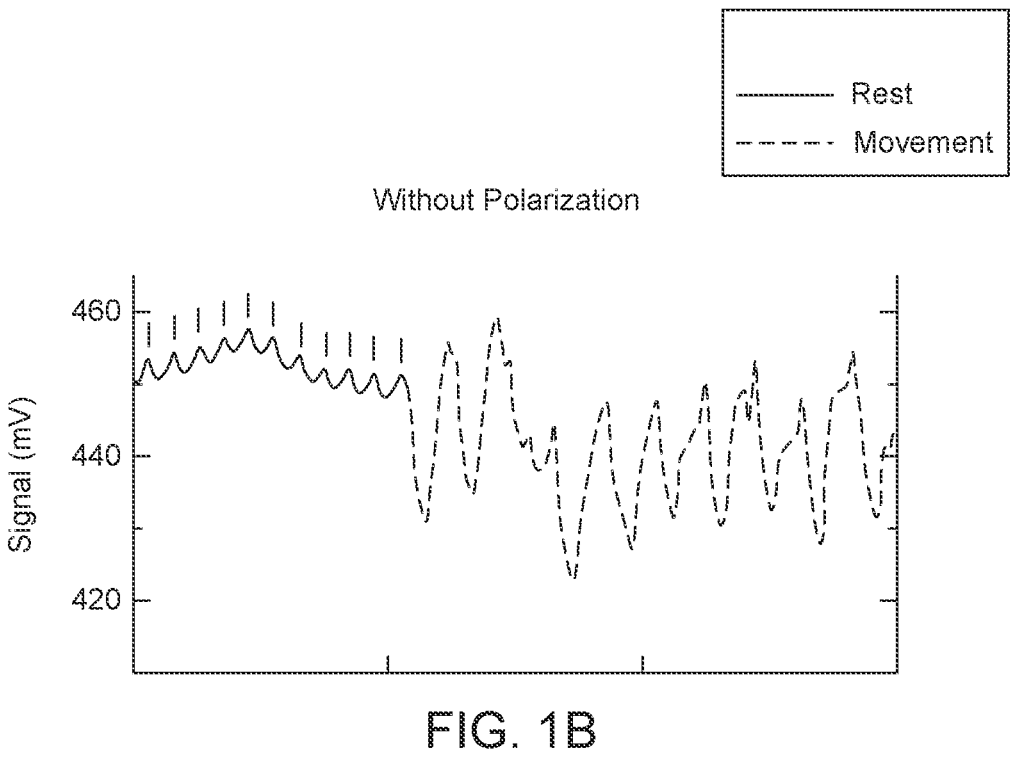
FIG. 1B illustrates detection of an electromagnetic signal without polarization, according to an embodiment.
Figure 1C:
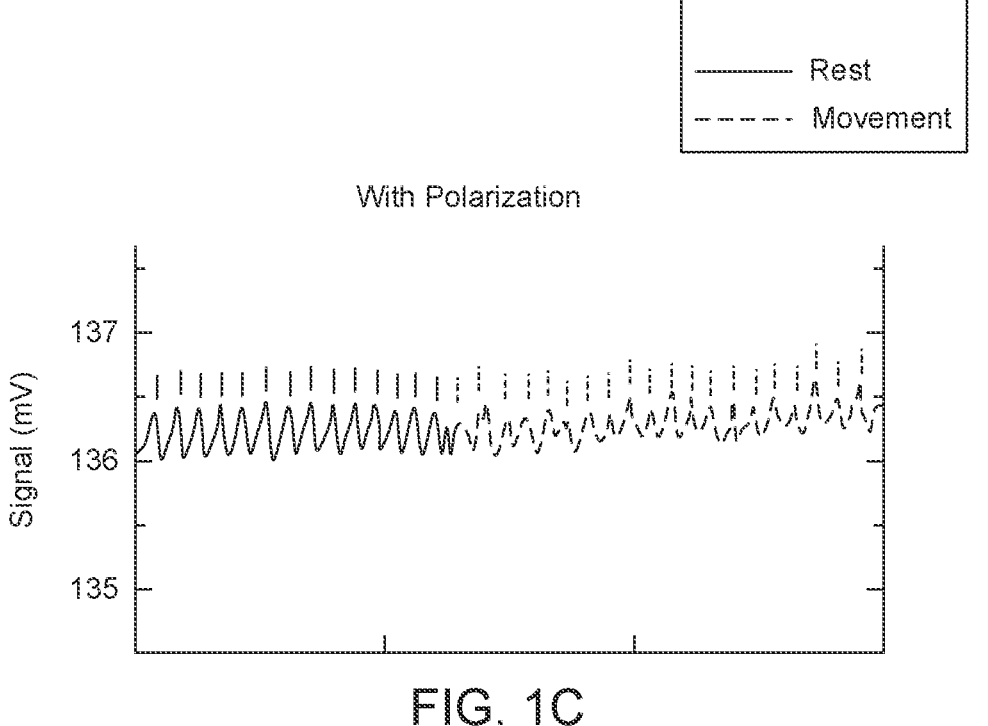
FIG. 1C illustrates detection of an electromagnetic signal with polarization, according to an embodiment.

FIG. 1B illustrates detection of an electromagnetic signal without polarization, according to an embodiment. FIG. 1C illustrates detection of an electromagnetic signal with polarization, according to an embodiment.

Referring to FIG. 1B, when an electromagnetic signal without polarization is detected, the amplitude of the detected signal varies significantly, and particularly when the source of the signal is moving.

Referring to FIG. 1C, when an electromagnetic signal with polarization is detected, the amplitude of the detected signal is relatively consistent, even when the source of the signal is moving.

The improved detection efficiency may also be referred to as an improved SNR or an improved SBR.

Figure 2:
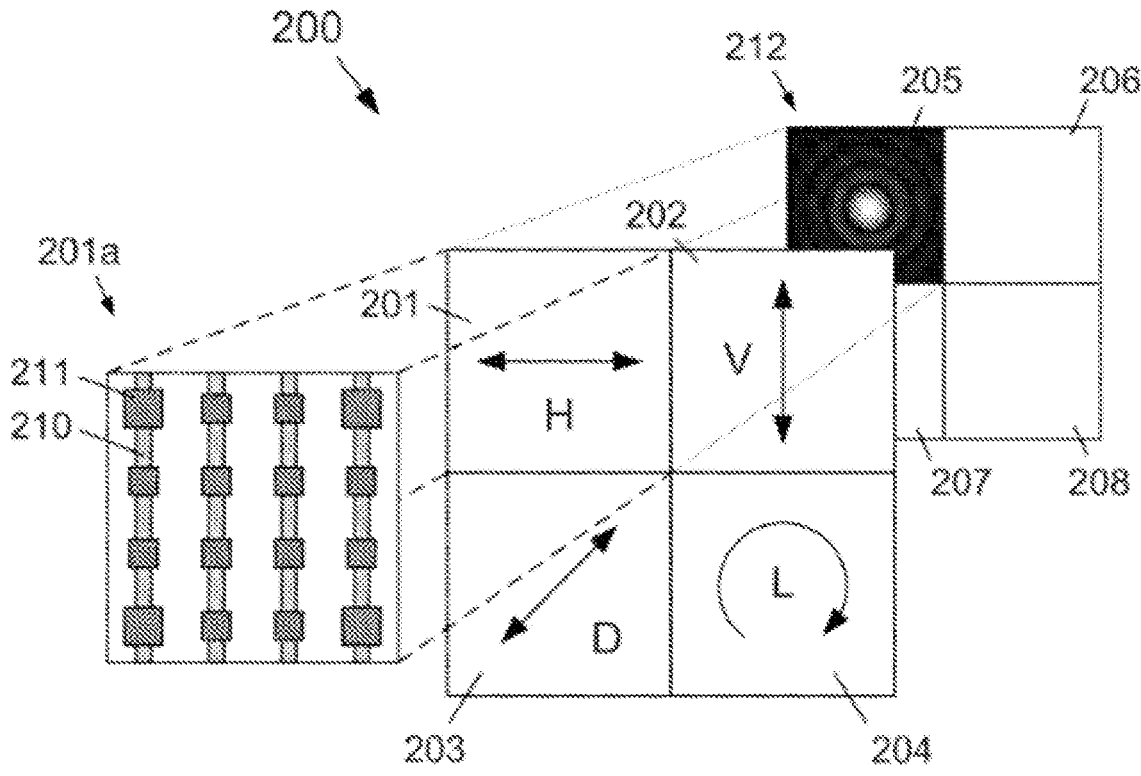
FIG. 2 illustrates an arrangement of four polarizing filters, according to an embodiment.

FIG. 2 illustrates an arrangement of four polarizing filters, according to an embodiment.

Referring to FIG. 2, the four polarizing filters 201-204 respectively correspond to the four pixels 205-208. Each respective pixel 205-208 includes a photodetector. The filter 201 horizontally polarizes light passing through the filter 201. The filter 202 vertically polarizes light. The filter 203 diagonally polarizes light, and the filter 204 circularly polarizes light. In an alternative embodiment, six polarizing filters and six pixels may be used. The additional two polarizing filters could be an anti-diagonally polarizing filter and a circularly polarizing filter that may polarize light in the opposite circular direction from the circularly polarizing filter 204.

Additional details of the polarizing filter 201 are provided at 201a, which depicts a top view of the polarizing filter 201. The polarizing filter 201 includes a wire grid 210, of which only one wire of the wire grid is indicated, one or more phase-modulating nanostructures or metasurfaces 211, of which only one nanostructure is indicated. The wires of the wire grid may include a metal-insulator-metal (MIM) structure that suppresses reflection from cross-polarization. The nanostructures 211 may be formed from a high dielectric index material, such as silicon (a Si, c Si, p-Si), silicon nitride ($Si_3N_4$), titanium dioxide ($TiO_2$), Gallium nitride (GaN), Zinc oxide (ZnO), hafnium silicate, zirconium silicate, hafnium dioxide and zirconium dioxide. The nanostructures 211 may also reduce the backscattering of the incident light, and may also help detect circular polarization.

The wire grid 210 horizontally polarizes the light passing through the polarizing filter, and the nanostructures 211 change, or modulate, the phase of the light that passes through the polarizing filter. The pattern of light that is generated by the polarizing filter 201 and that is focused on the pixel 205 is depicted at 212. The other polarizing filters 202-204 also include a wire grid having a series of MIM structures and one or more nanostructures. The nanostructures of the circularly polarizing filter 204 provide a 90-degree phase shift so that the circularly polarizing filter operates as a quarter wave plate. The nanostructures may modify wavelengths and be positioned with thin films to provide spacing for the nanostructures. The pixels may have additional antireflective thin film layers and microlens to improve the light collection.

The arrangement 200 of the four polarizing filters 201-204 and the four pixels 205-208 may be used to generate the following six polarization states for incident light, shown in Equations (1)-(6), below.

$$I_H = I_H \qquad \text{Equation (1)}$$

$$I_V = I_V \qquad \text{Equation (2)}$$

$$I_D = I_D \qquad \text{Equation (3)}$$

$$I_A = I_H + I_V - I_D \qquad \text{Equation (4)}$$

$$I_R = I_H + I_V - I_L \qquad \text{Equation (5)}$$

$$I_L = I_L \qquad \text{Equation (6)}$$

in which $I_H$ is the light intensity parameter of horizontally polarized light (H) measured at pixel 205, $I_V$ is the light intensity parameter of the vertically polarized light (V) measured at pixel 206, $I_D$ is the light intensity parameter of the diagonally polarized light (D) measured at pixel 207, $I_A$ is the intensity parameter of the anti-diagonally polarized light, $I_R$ is the intensity parameter of the right-hand circularly polarized light, and $I_L$ is the light intensity parameter of the left-hand circularly polarized light (L) measured at pixel 208.

Using the intensity parameters of Equations (1)-(6), the Stokes parameters S0, S1, S2 and S3 may be calculated as follows, as shown below in Equations (7)-(14).

$$S_0 = I_H + I_V \qquad \text{Equation (7)}$$

$$S_1 = I_H - I_V \qquad \text{Equation (8)}$$

$$S_2 = 2 * I_D - S_0 \qquad \text{Equation (9)}$$

$$S_3 = 2 * I_L - S_0 \qquad \text{Equation (10)}$$

$$DoLP = sqrt(S_1^2 + S_2^2)/S_0 \qquad \text{Equation (11)}$$

$$AoLP = 0.5 * tan^{-1} * S_2/S_1 \qquad \text{Equation (12)}$$

$$DoCP = S_3/S_0 \qquad \text{Equation (13)}$$

$$AoCP = 0.5 * sin^{-1} * S_3/S_1 \qquad \text{Equation (14)}$$

in which DoLP is the degree of linear polarization, AoLP is the angle of linear polarization, DOCP is the degree of circular polarization, and AoCP is the angle of circular polarization.

Figure 3:
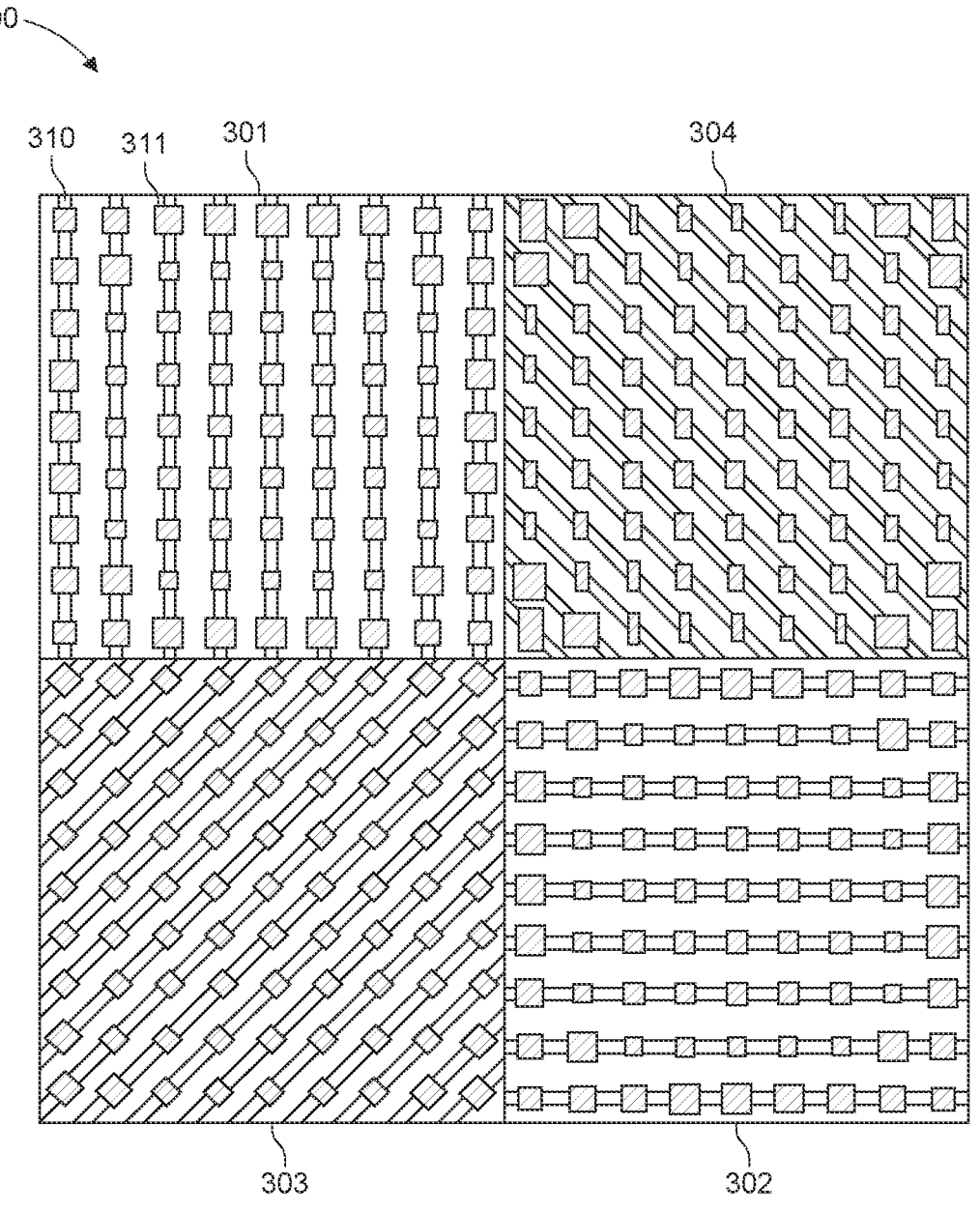
FIG. 3 illustrates a top view of a polarizer, according to an embodiment.

FIG. 3 illustrates a top view of a polarizer, according to an embodiment.

Referring to FIG. 3, the polarizer 300 may detect up to six polarization states. The polarizer 300 includes four polarizing filters 301-304 that each corresponds to (or are mapped to) a pixel of an image sensor. The filter 301 horizontally polarizes light passing through the filter 301. The filter 302 vertically polarizes light. The filter 303 diagonally polarizes light, and the filter 304 circularly polarizes light.

Each of the filters 301-304 include a wire grid 310 having an MIM structure and one or more phase-modulating nano-structures 311, although the wire grid and the phase-modulating nanostructures are only indicated for the filter 301. The horizontal and vertical dimensions of the phase-modulating nanostructures 311 may be varied based on the graph 300 in FIG. 3 to achieve a desired amount of focusing. For example, the phase-modulating nanostructures 311 may be depicted as being generally square or circular for the polarizing filters 301-303, but having different horizontal and vertical dimensions (e.g., rectangular or ellipsoidal) depending upon the position of the nanostructure on the polarizing filter. The phase-modulating nanostructures of the circularly polarizing filter 304 may be generally rectangular or ellipsoidal depending upon the position of the nanostructure on the polarizing filter.

The arrangement of the polarizing filters 301-304, in which the horizontally polarizing filter 301 is in the upper-left corner of the polarizer 300, the vertically polarizing filter 302 in the lower-right corner, the diagonally polarizing filter 303 in the lower-left corner, and the circularly polarizing filter 304 is in the upper-right corner, is an example arrangement and other arrangements are possible. In another example embodiment, two additional polarizing filters, such as an anti-diagonally polarizing filter and a circularly polarizing filter that would polarize light in the opposite circular direction from the circularly polarizing filter 304, may be included in the polarizer 300. Such an embodiment could also use two additional pixels. The polarizer 300 may correspond to a super pixel, as discussed below with reference to FIGS. 7-10.

Figure 4:
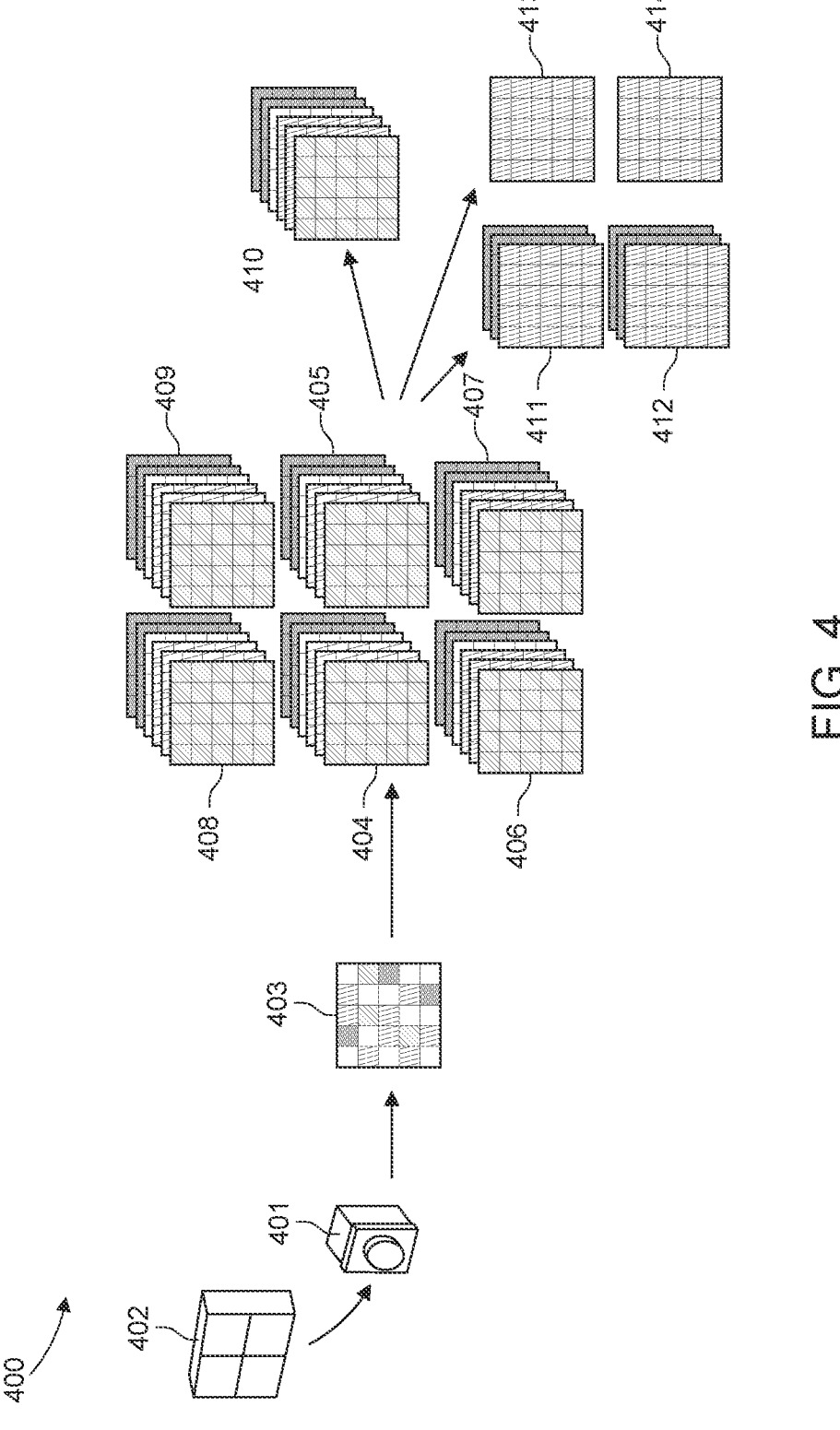
FIG. 4 illustrates a multispectral and polarization sensing system, according to an embodiment.

FIG. 4 illustrates a multispectral and polarization sensing system, according to an embodiment.

Referring to FIG. 4, the multispectral and polarization sensing system 400 enables the detection of both polarization and spectral information. The multispectral and polarization sensing system 400 may include polarizing filters and spectral filters that provide on-chip simultaneous full Stokes polarization parameters (both linear and circular polarization) and multi/hyper spectral imaging. The multispectral and polarization sensing system 400 may include a camera 401 having a sensor or a photodiode.

Furthermore, the multispectral and polarization sensing system 400 may detect images from an array of pixels (2D signal information, referred to as an "image") or light irradiated in one or more pixels (1D signal information, referred to as a "signal"). The multispectral and polarization sensing system 400 may include polarizing and spectral filters 402. A 1D signal or 2D image captured by the camera 401 having a sensor or a photodiode may be processed as a grayscale image 403 and de-mosaiced. Additionally, the captured 1D signal or 2D image may be processed to generate corresponding multispectral linear and circularly polarized light that passes through the polarizing and spectral filters 402. For example, depending upon the particular polarizing and spectral filters 402 that are used, the captured 1D signal or 2D image may generate multispectral horizontally polarized images 404, multispectral vertically polarized images 405, diagonally (45 degrees) polarized images 406, anti-diagonally polarized images 407, right-hand circularly polarized images 408, and left-hand circularly polarized images 409. Parameters determined from the linearly and circularly polarized images 404-409 may be used to generate full Stokes parameters for the light of the image.

Further, the captured 1D signal or 2D image may be processed to generate non-polarized multispectral signals or images 410, and/or red (R), green (G) and blue (B) images 411. If the multispectral filters include filters for infrared (IR), multispectral IR images 412 may be generated by the imaging system 400. Signals or images may be generated that indicate the degree of linear polarization (DoLP) 413 and the degree of circular polarization (DoCP) 414 may also be generated.

Accordingly, polarization information and spectral information may be generated based on the multispectral and polarization sensing system 400 of FIG. 4.

Figure 5A:
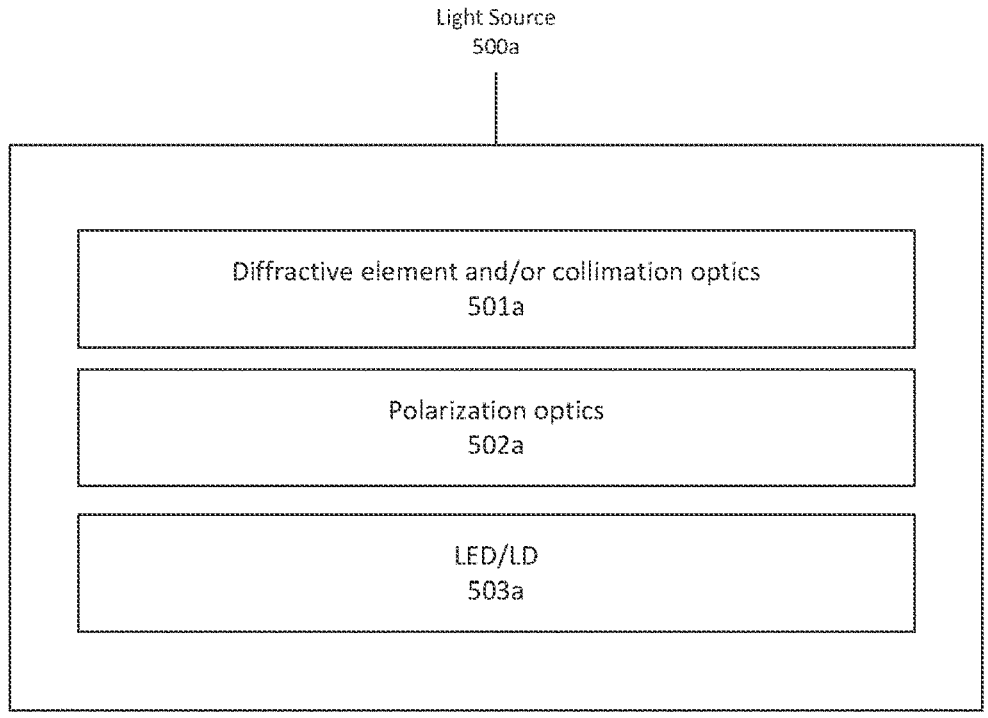
FIGS. 5A and 5B respectively illustrate a light source and a sensor, according to various embodiments.
Figure 5B:
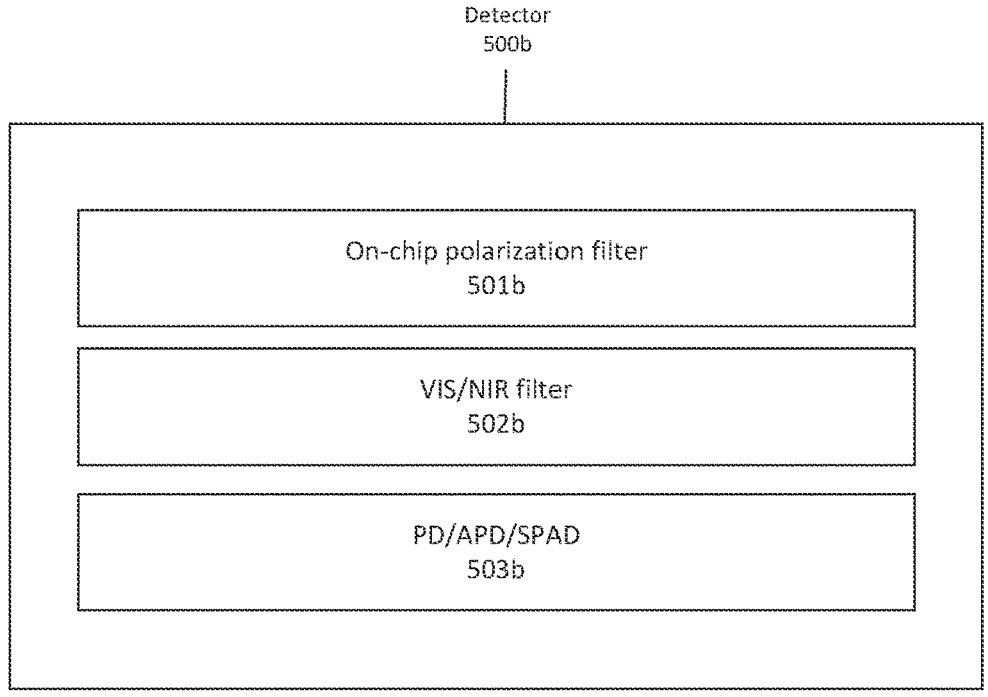

FIGS. 5A and 5B respectively illustrate a light source and a sensor, according to various embodiments.

At least some or all of the light source 500a of FIG. 5A and the detector 500b of FIG. 5B may be combined to form a PPG sensor.

Referring to FIG. 5A, a light source 500a is provided. The lights source 500a includes a diffractive element and/or collimation optics 501a (a collimation optical element), polarization optics 502a (a polarization optical element), and an LED/LD 503a (additionally, other light emitting elements may be used (e.g., a vertical-cavity surface-emitting laser (VCSEL))) (an electromagnetic spectral emission source). The diffractive element and/or collimation optics 501 may be combined as one element or separated as two separate elements, where the collimation optical element focuses or collimates an electromagnetic spectral emission into a narrow or tight beam (e.g., reduces the size (e.g., a diameter, circumference, or width) of the beam) to reduce diffusion, and the diffractive optical element may separate the electromagnetic spectral emission into a predetermined arrangement (e.g., lines, dots, or patterns). The diffractive element and/or collimation optics 501a and the polarization optics 502a may be combined with (or added to) the LED/LD 503a so that the amount energy of light that is reflected back (e.g., reflected back from a user's skin) is increased. The LED/LD 503a may emit light with frequencies in a visible range and/or a near infrared (NIR) spectrum.

The diffractive element and/or collimation optics 501a may improve the efficiency input light by reducing the diverging aspects of the input light. The diffractive element and/or collimation optics 501a may be configured to produce different types of outputs for the input light. For example, the diffractive element and/or collimation optics 501a can diffract (or separate) the input light into lines, dots, a matrix pattern, or other predetermined arrangements. In this manner, the input light may be diffracted to a specific region or area causing that specific region or area to have a higher concentration of the light's energy. The polarization optics 502a may control the input coefficient of the light.

Referring to FIG. 5B, the detector 500b is provided. Signals (e.g., light) having different spectrum interact differently with target molecules, biomarkers and health relevant parameters. For example, blue may be used for detecting antioxidant levels, like beta carotene; green may be used for pulse rate monitoring because it is less influenced by the tissue and vein region than other colors and/or spectra. Red and IR may be used by determining a difference in absorbance at those two frequencies (a red frequency versus an IR frequency) between oxygenated and unoxygenated hemoglobin. Using the difference in these two frequencies allows the concentration of oxyhemoglobin to be calculated (e.g., the red LED may be at the frequency where oxyhemoglobin and hemoglobin have identical absorbances).

The detector 500b includes a polarization filter 501b, a VIS/NIR filter 502b, and a PD/APD/SPAD 503b. The polarization filter 501b may include a polarization filter array. The VIS/NIR filter 502b may be an electromagnetic spectrum filter and may include a color filter either organic or inorganic, a nanostructured color filter, a narrow band filter, distributed Bragg filters or a broadband filter. Some or all of the filters and/or components in the VIS/NIR filter 502b may be made of a stack of semiconductor(s) and/or oxides/nitride. For example, each of the filters included in the VIS/NIR filter 502b may be included in a stack of semiconductors but for the color filter. In addition, the VIS/NIR filter 502b may detect signals that penetrate more deeply into the skin due to less scattering.

The PD/APD/SPAD 503b may include a sensor, which allows the detector 500b to measure both spectral light information and polarized light information. PD, APD, and SPAD sensors may have different sensitives, which may improve (e.g., reduce) SNR for detecting signals for different applications. For example, SPAD may work well with a laser input signal, where PD and APD may work better with an LED input signal. In addition, different linear polarized light may interact differently with different bodily materials (e.g., fat, blood, or arteries). Circular polarized light may interact differently with molecules like skin cancer melanoma, antioxidants, triglyceride and so on.

Accordingly, the detector 500b may be sensitive to polarization calibration and spectrum calibration. In addition, the polarization filter 501b may include aluminum (Al), titanium oxide (TiO2), aluminum oxide (Al2O3), tungsten (W), silicon oxide (SiO2), silicone (Si), silicon nitride (Si3N4), and amorphous silicon (a-Si).

Figure 6:
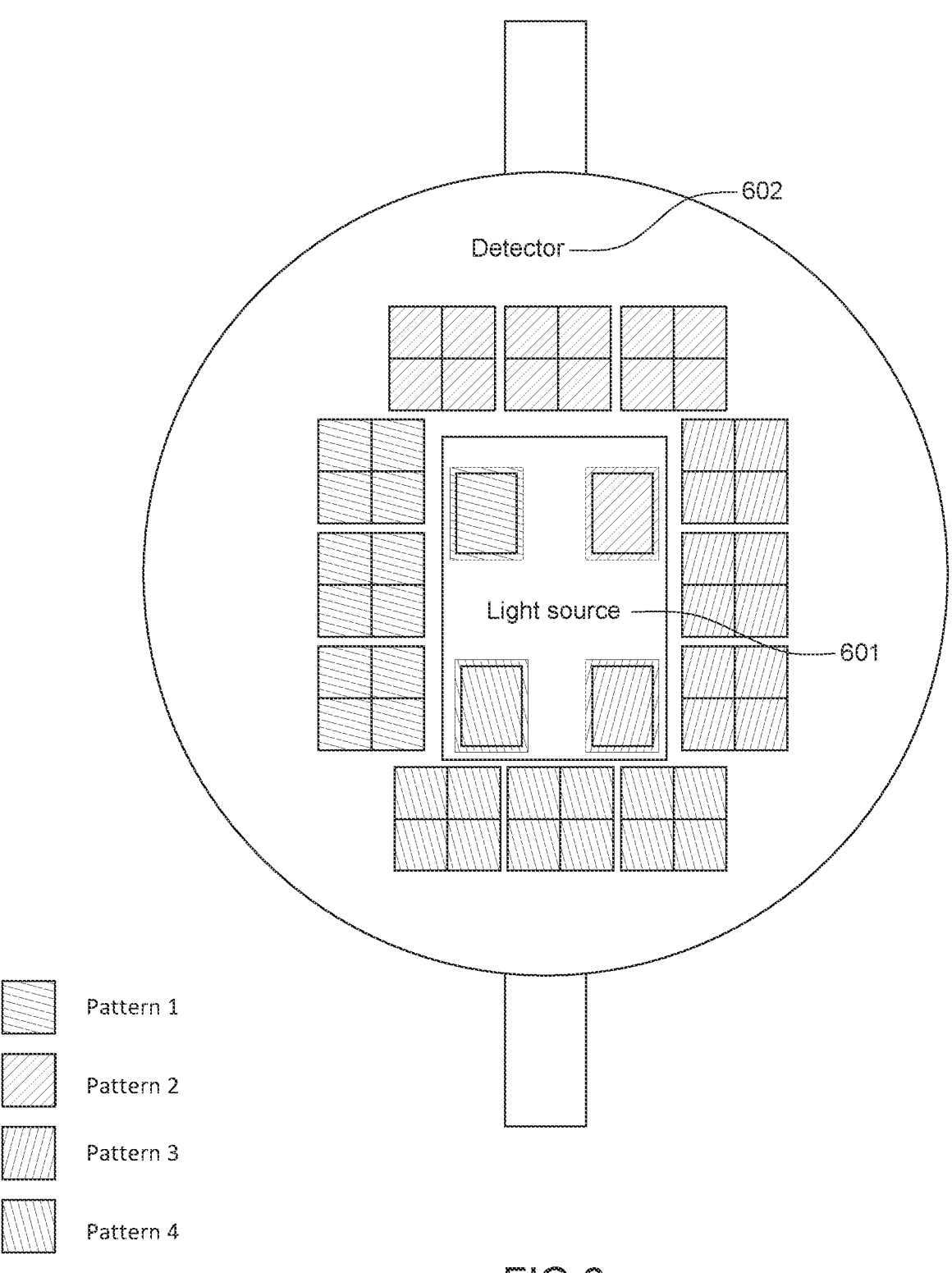
FIG. 6 illustrates a PPG sensor configuration, according to an embodiment.

FIG. 6 illustrates a PPG sensor configuration, according to an embodiment.

Referring to FIG. 6, the PPG sensor 600 includes a light source 601 and a detector 602.

The light source 601 includes four light emitting elements. Each of the light emitting elements may correspond to different spectrums (e.g., different colors). Light emitting elements having different spectral characteristics advantageously behave differently when they come into contact with an object (e.g., a user's skin). This advantage may be used for single color pixel targeting by light emitting elements emitting wavelengths using on-chip polarizer filters. The light emitted from the light emitting elements may each have a narrow bandwidth (e.g., a single color) or a wide bandwidth (e.g., covering visible light all the way to infrared (IR) light).

The detector 602 is made up of a number of super pixels in proximity to the light source 601. Each of the super pixels in the detector 602 may include features of the polarizer 300 of FIG. 3. That is, each of the super pixels in the detector 602 may include four distinct pixels (e.g., portions of the super pixel) that are each capable of filtering light differently, such as how light is filtered by polarizing filters 301-304 (corresponding to pixels), to collect light polarization information. Additionally, each super pixel may include more than four pixels (e.g., six) to collect spectral information and light polarization information.

Furthermore, each super pixel may be designed to detect light of a predetermined frequency (corresponding to a spectrum of one of the four light emitting elements), as distinguished by the patterns illustrated in FIG. 6. That is, a first pattern type may correspond to a first spectrum, a second pattern type may correspond to a second spectrum, a third pattern type may correspond to a third spectrum, and a fourth pattern type may correspond to a fourth spectrum.

Additionally, the distribution (e.g., physical arrangement) of the super pixels on the left side to the light source 601 is shown to be vertical (e.g., a vertical distribution of 3 super pixels). The distribution of the super pixels may enable the PPG sensor to determine a depth at which the detected light penetrates, as well as other characteristics based on the distribution. For example, the super pixels having a first pattern type corresponding to the first spectrum may identify light output from the light emitting element having the first pattern type corresponding to the first spectrum of the light source 601 based on an angle of the detected light at each of the super pixels. Since the light having the first spectrum is output at a particular area of the light source, the super pixels capable of detecting the light having the first spectrum may be arranged so that some of the super pixels detect the light having the first spectrum at different angles than others. The angle information may be used to determine the depth at which the light penetrates. Additionally, a time difference from which the light is detected by a first super pixel at a first location and a second super pixel at a second location may be used to determine the angle information.

The arrangement of the super pixels and their corresponding light emitting elements (e.g., super pixels and light emitting element for the first spectrum having the first pattern, super pixels and light emitting element for the second spectrum having the second pattern, etc.) are not limited to that which is shown. Many different alternative arrangements are possible which may be capable of detecting different characteristics of the light due to the alternative arrangements. Thus, the light source and detector arrangements of the PPG sensors can be designed to satisfy particular light detection characteristics that are sought by the design.

Data produced by the PPG sensors may be processed in an application processor on the same platform (e.g., a chip) or in the cloud.

Figure 7:
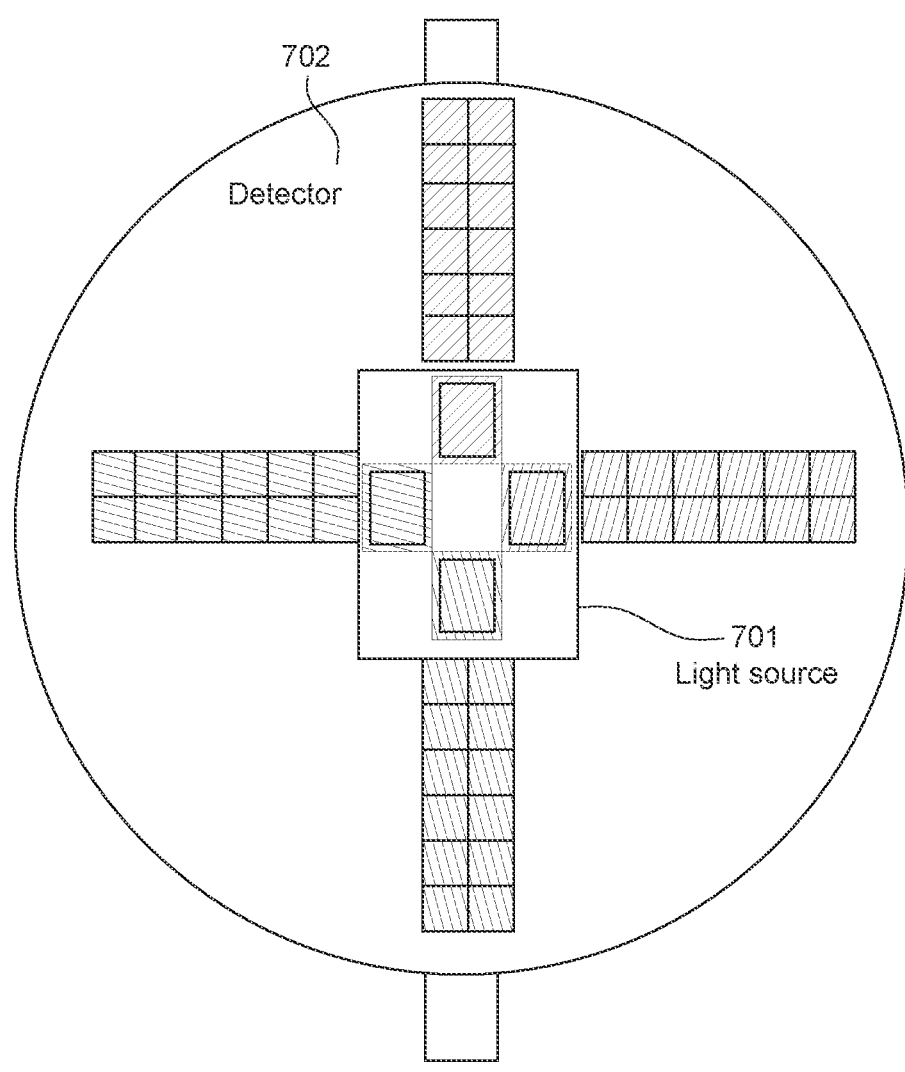
FIG. 7 illustrates a PPG sensor configuration, according to an embodiment.
Figure 7:
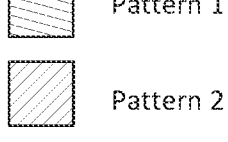
Figure 7:
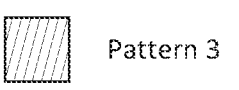
Figure 7:

FIG. 7 illustrates a PPG sensor configuration, according to an embodiment.

Referring to FIG. 7, the PPG sensor 700 includes a light source 701 and a detector 702.

FIG. 7 includes a number of characteristics that are similar to FIG. 6. For example, the light source includes four light emitting elements having different light spectrums (corresponding to the four different patterns). However, unlike FIG. 6, FIG. 7 shows each set of super pixels corresponding to each light spectrum to be oriented as straight lines facing outward from the light source. The super pixels are shown as forming lines at approximately 0, 90, 180, and 270 degrees, however other arrangements are possible depending on the design requirements of the PPG sensor. For example, super pixel lines may be oriented at 45, 135, 225, and 315 degrees. In addition, multiple sets of super pixels may be added, thereby increasing the total number of super pixels. Like FIG. 6, the super pixels of FIG. 7 are each made up of at least four pixels to detect different polarity characteristics of the light emitted from the light source.

Since some of the super pixels are arranged farther away from the light source in FIG. 7 than compared to FIG. 6 (where each of the super pixels are arranged around the light source), the super pixels in FIG. 7 arranged farther away may be able to detect larger angles of the reflected light emitting from the light source. Generally, larger angles are associated with larger depths. However, for the super pixels that are arranged far away from the light source, sensitivity of the detected light may be lower as compared to super pixels arranged closer to the light source.

Figure 8:
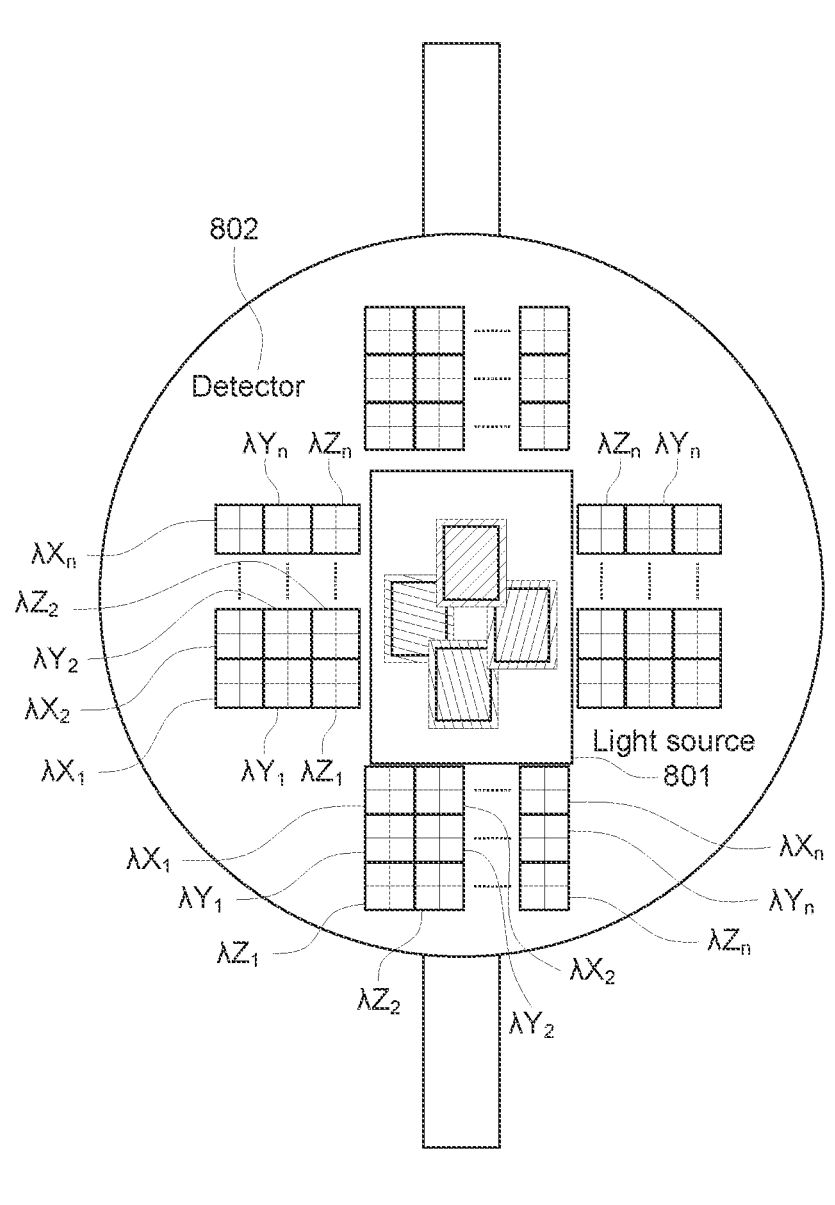
FIG. 8 illustrates a PPG sensor configuration, according to an embodiment.

FIG. 8 illustrates a PPG sensor configuration, according to an embodiment.

Referring to FIG. 8, the PPG sensor 800 includes a light source 801 and a detector 802.

The super pixels of the detector 802 each include a number of pixels (e.g., four), similar to FIGS. 6-7. For example, the super pixels shown in detector 802 include a λ (generally corresponding to a wavelength), a variable (e.g., "x", "y", or "z"), and a number. The super pixels are incrementally listed. For example, a top row of super pixels are incrementally listed: "λx1", λx2" . . . "λxn", where n represent the total number of super pixels in this grouping. The variable "x" may correspond to a spectral range (e.g., a spectral range for blue light). Thus, the combination of the "λx1", λx2" . . . "λxn" super pixels may be very sensitive to detecting particular spectral ranges of the blue light. Furthermore, the "y" variable may correspond to a different spectral range (e.g., a spectral range for green light), and the "z" variable may also correspond to a different spectral range (e.g., a spectral range for red light). Accordingly, each set of super pixels may be designed to precisely capture and identify light having a wide spectral range.

Since the super pixels of the detector 802 are each capable of detecting many different spectrums of lights, the light emitting elements in the light source should be arranged to ensure that each light emitting element is capable of emitting (powerful or proximate enough to emit) light to the pixels at each super pixel for detection.

Figure 9:
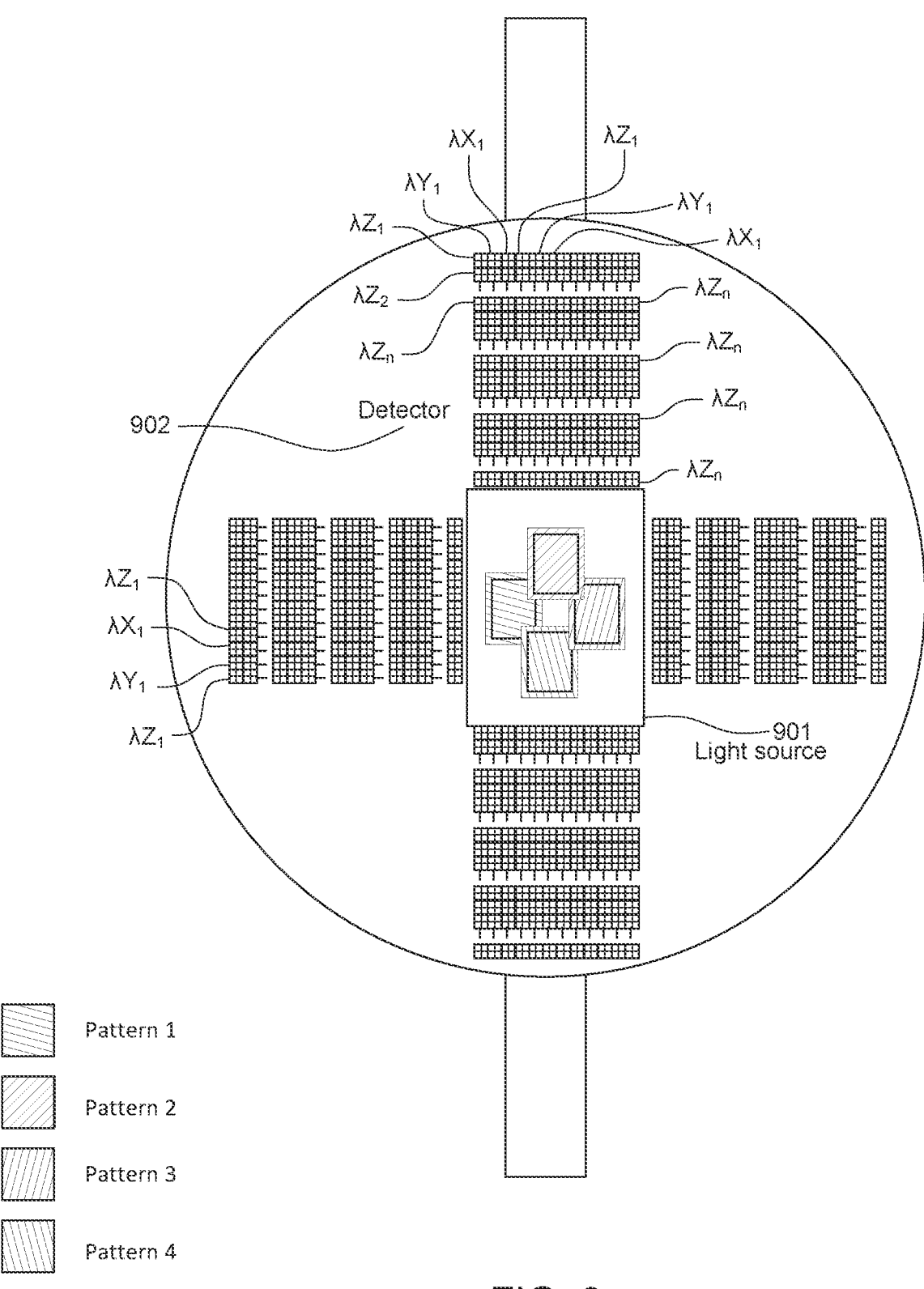
FIG. 9 illustrates a PPG sensor configuration, according to an embodiment.

FIG. 9 illustrates a PPG sensor configuration, according to an embodiment.

Referring to FIG. 9, the PPG sensor 900 includes a light source 901 and a detector 902.

FIG. 9 is substantially similar to FIG. 8, with a difference being that a plurality of wide spectral range super pixels are provided in an array like pattern in the detector 902 on each side of the light source 901. The array like pattern may improve the accuracy of what particular area of the detector 902 light is detected at.

Figure 10:
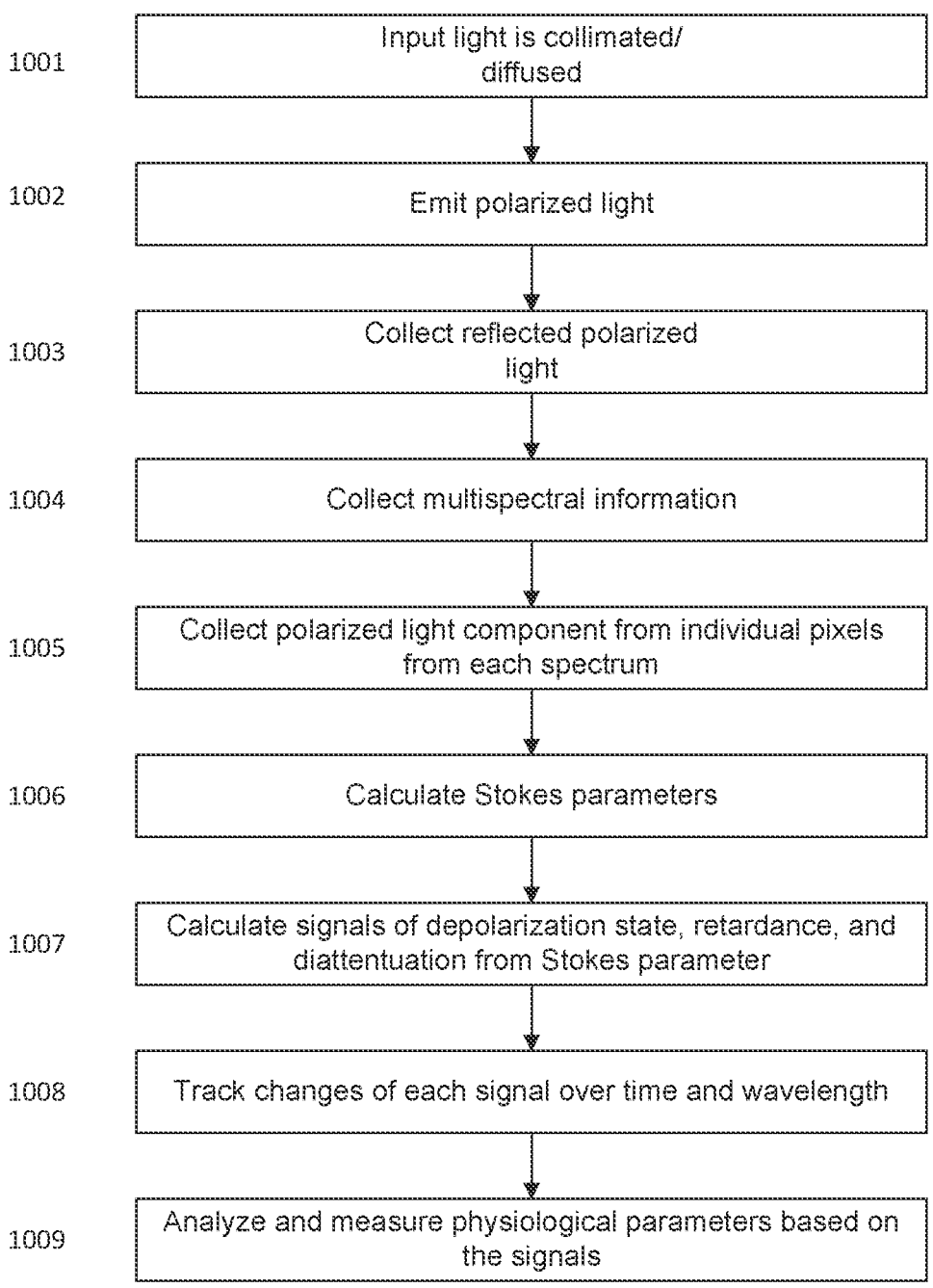
FIG. 10 illustrates a flowchart for biosignal detection and analysis, according to an embodiment.

FIG. 10 illustrates a flowchart for biosignal detection and analysis, according to an embodiment. It is noted that the method in FIG. 10 may include more or less steps, and the method is not limited to the steps that are shown. Additionally, some or all steps may be performed in parallel or in a different order than what is shown.

Referring to FIG. 10, at step 1001, input light is collimated or diffused. Accordingly, the input light can be separated into lines, dots, a matrix pattern, or other predetermined arrangements. In this manner, the input light may be diffracted to a specific region or area causing that specific region or area to have a higher concentration of the light's energy.

At step 1002, polarized light (e.g., an electromagnetic spectrum emission) is emitted. For example, the input light that is collimated or diffused may be emitted by a light source in an electronic device.

At step 1003, the emitted polarized light is reflected off of a surface and collected. For example, as described above, a sensor featuring four pixels included in an electronic device may collect the reflected polarized light. The surface may be living tissue and may include multiple surfaces therein. For example, the polarized light may be reflected off of skin, with some of the light being reflected off an epidermis layer of the skin and some of the light being reflected off of a dermis layer of the skin. In addition, some of the polarized light may be reflected by blood arteries, and molecules included therein.

At step 1004, multispectral information of the reflected polarized light is collected. This may include polarized light having different wavelengths or frequencies. In addition, polarized light within predefined wavelength or frequency ranges may be collected.

At step 1005, a polarized light component of individual pixels from each of the spectrums is determined.

At step 1006, the Stokes parameters (e.g., S0, S1, S2, and S3) are calculated, and all six polarization states ($I_H$, $I_V$, $I_D$, $I_L$, $I_A$, and $I_R$) may be determined. These values may be used to identify particular molecules or parameters of the surface which the polarized light is reflected.

At step 1007, at least one additional signal is calculated based on the Stokes parameters, such as depolarization state information, retardance information, and diattenuation information.

At step 1008, the additional signal is tracked over time or wavelength. That is, a first intensity or amplitude of the additional signal may be determined at a first time point, a second intensity or amplitude of the additional signal may be determined at a second time point after the first time point, etc.

At step 1009, the additional signal is analyzed and measured to reveal physiological parameters (e.g., heart-rate information, respiratory rate information, hypertension signatures, red blood cell concentration information, blood saturation information, a continuous blood pressure, pulse rate information, a pulse pressure, cardiovascular conditions, stroke volume information, cardiac output information, a one lead electrocardiogram (ECG), a systematic vascular resistance, cardiac index, a mean arterial pressure, antioxidants, melanoma information, triglyceride information, cholesterol information, and beta carotene information) related to the surface from which the polarized light is reflected.

Figure 11:
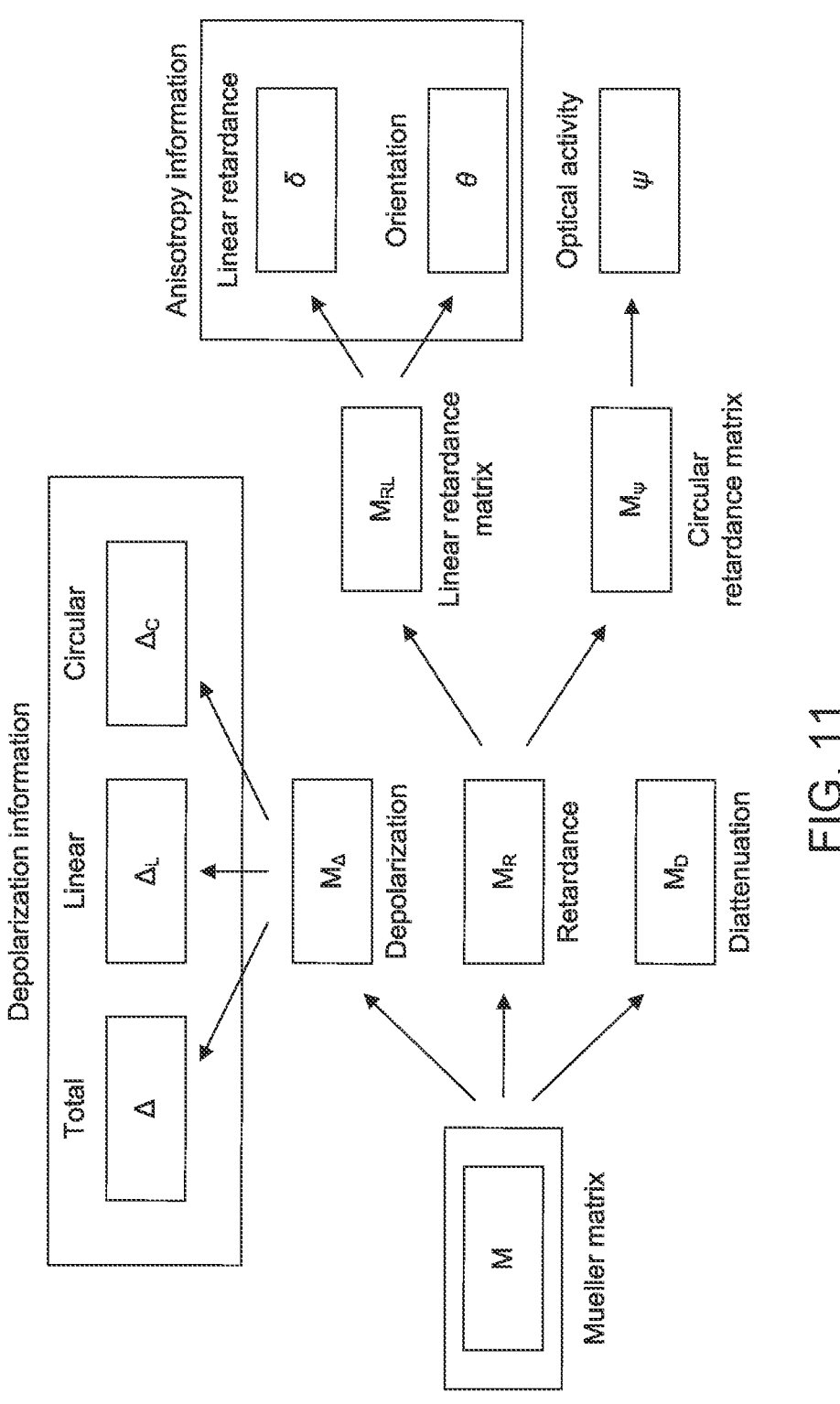
FIG. 11 illustrates a relationship among parameters that may be used to process a signal calculated based on reflected polarized light, according to an embodiment.

FIG. 11 illustrates a relationship among parameters that may be used to process a signal calculated based on reflected polarized light, according to an embodiment.

Referring to FIG. 11, a Mueller matrix M may be applied to the Stokes parameters to obtain at least one of information related to depolarization $M_A$ retardance $M_R$ and/or diattenuation $M_D$.

Depolarization $M_A$ may refer to the magnitude (or amount) of polarization and can include linear depolarization information $\Delta_L$, circular depolarization information $\Delta_C$ and/or total depolarization information $\Delta$.

Retardance $M_R$ may refer to the magnitude (or amount) of an optical path difference (e.g., a phase shift) experienced by polarized light. The retardance $M_R$ may include a linear retardance matrix $M_{RL}$ to identify anisotropy information, including a linear retardance $\delta$ and an orientation $\theta$ to identify a degree and angle of polarization. Retardance $M_R$ may also be calculated with circular polarization using a circular retardance matrix $M_\psi$ to identify optical activity $\psi$ (e.g., the direction of the circular polarization (e.g., clockwise or counterclockwise)).

Diattenuation $M_D$ may refer to the intensity of the signal with respect to a polarization state. Accordingly, diattenuation $M_D$ may indicate one or more ratios of intensities of different polarization states.

According to an embodiment, a method for biosignal detection and analysis may use polarized microscopy to improve SNR and measure antioxidants. For example, S0 may represent the intensity of the light (polarized+unpolarized); S1 may represent the intensity of linear horizontal or vertical polarization; S2 may represent the intensity of linear +45° or −45° polarization; and S3 may represent the intensity of right or left circular polarization. Accordingly, using the Stokes parameters S0-S3, a signal may be calculated based on reflected polarized light to identify, for example, characteristics of a target molecule that is beneath a surface having a defined thickness.

Different types of polarized light (e.g., linear polarized light, circular polarized light) can be used to reveal different characteristics about the surface from which it is reflected. For example, unpolarized light and polarized light having intensities of $I_0°$ and $I_{45}°$ and $I_{90}°$ may each be emitted and reflected off of a surface. The unpolarized light typically does not penetrate surfaces well, and therefore produces a relatively low quality SNR. $I_{90}°$ polarized light may penetrate surfaces better than the unpolarized light, thereby having a better SNR. Additionally, if $I_0°$ and $I_{45}°$ and $I_{90}°$ polarized light are each emitted, reflected, and measured, then the resulting SNR may be better than the $I_{90}°$ polarized light, since Stokes parameters for each of the different types of polarized light may be applied.

In addition, different molecules may be sensitive to different types of polarized light. For example, a beta carotene molecule is highly sensitive to circular polarization and, therefore, beta carotene can be detected by comparing the DoLP with the DoCP. In other words, since beta carotene is highly sensitive to circular polarization and is not sensitive to linear polarization, the DoCP may reveal the existence of beta carotene molecules by detecting the circular polarization intensity at different wavelengths. For example, a peak to trough (valley) ratio of the DoCP may be calculated for a predefined wavelength range to assess the likelihood that beta carotene is present. Generally, the larger the wavelength range, the more accurate the detection will be.

Additionally, the different types of polarized light can be used to reveal cardiovascular signatures and information about blood, fat, arteries, and tendons.

Figure 12:
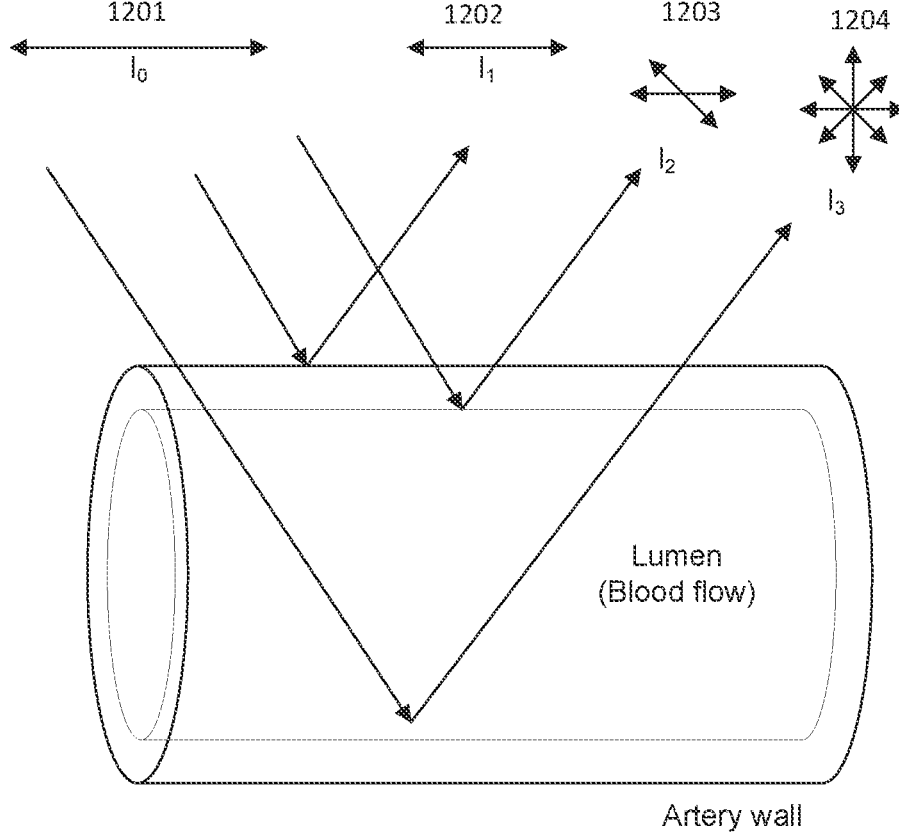
FIG. 12 illustrates polarized light penetrating a blood artery, according to an embodiment.

FIG. 12 illustrates polarized light penetrating a blood artery, according to an embodiment.

Referring to FIG. 12, a plurality of types of polarized light are emitted towards a blood artery. Since the different types of polarized light 1201 feature different characteristics, detecting the different types of polarized light may reveal information necessary to calculate biosignals at different depths. For example, linear polarized light having one angle of polarization 1202 may be reflected off of an outer surface of the artery wall, linear polarized light having two angles of polarization 1203 may penetrate the artery wall and may. be reflected off of a first inner surface of the artery wall, and linear polarized light having four angles of polarization 1204 may penetrate even further and be reflected off of a second inner surface of the artery wall.

After detection, Stokes parameters may be calculated for each of the reflected and detected types of polarized light 1202, 1203, and 1204 to determine biosignals for the respective depths of penetration of the polarized light. The polarized light may be used, for example, to detect a wall-to lumen ratio of retinal arterioles as a tool to assess vascular changes, since a thickness of the artery wall relative to the thickness of the lumen may indicate health-related information.

Thus, as described above, methods and systems are provided for using a polarized light source and multispectral full Stokes polarization PPG sensors to identify biosignals and other health related information. In addition, simultaneously modulating the phase and polarization of the light may improve SBR and field of view (FOV) properties. Accordingly, spectral sensitive physiological parameters and molecular information (e.g., antioxidant information, triglyceride information, cholesterol information, etc.) can be identified based on detecting the different types of polarized light reflected off of a surface of a living tissue (e.g., skin).

Figure 13:
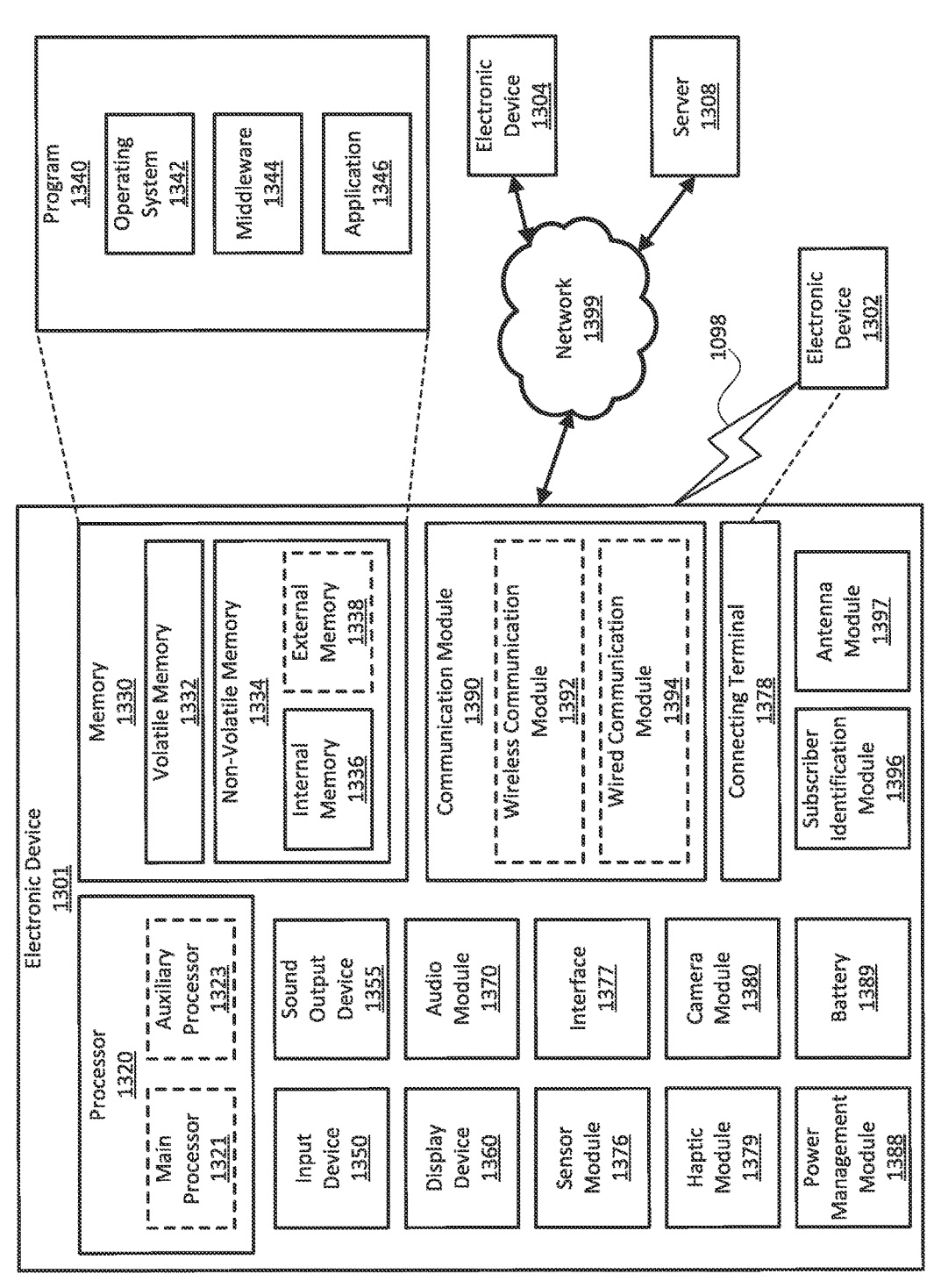
FIG. 13 illustrates an electronic device in a network environment, according to an embodiment.

FIG. 13 illustrates an electronic device in a network environment, according to an embodiment.

Referring to FIG. 13, the electronic device 1301, e.g., a mobile terminal including GPS functionality, in the network environment 1300 may communicate with an electronic device 1302 via a first network 1398 (e.g., a short-range wireless communication network), or an electronic device 1304 or a server 1308 via a second network 1399 (e.g., a long-range wireless communication network). The electronic device 1301 may communicate with the electronic device 1304 via the server 1308. The electronic device 1301 may include a processor 1320, a memory 1330, an input device 1350, a sound output device 1355, a display device 1360, an audio module 1370, a sensor module 1376, an interface 1377, a haptic module 1379, a camera module 1380, a power management module 1388, a battery 1389, a communication module 1390, a subscriber identification module (SIM) 1396, or an antenna module 1397 including a GNSS antenna. In one embodiment, at least one (e.g., the display device 1360 or the camera module 1380) of the components may be omitted from the electronic device 1301, or one or more other components may be added to the electronic device 1301. In one embodiment, some of the components may be implemented as a single integrated circuit (IC). For example, the sensor module 1376 (e.g., a fingerprint sensor, an iris sensor, or an illuminance sensor) may be embedded in the display device 1360 (e.g., a display).

The processor 1320 may execute, for example, software (e.g., a program 1340) to control at least one other component (e.g., a hardware or a software component) of the electronic device 1301 coupled with the processor 1320, and may perform various data processing or computations. As at least part of the data processing or computations, the processor 1320 may load a command or data received from another component (e.g., the sensor module 1376 or the communication module 1390) in volatile memory 1332, process the command or the data stored in the volatile memory 1332, and store resulting data in non-volatile memory 1334. The processor 1320 may include a main processor 1321 (e.g., a central processing unit (CPU) or an application processor, and an auxiliary processor 1323 (e.g., a graphics processing unit (GPU), an image signal processor (ISP), a sensor hub processor, or a communication processor (CP)) that is operable independently from, or in conjunction with, the main processor 1321. Additionally or alternatively, the auxiliary processor 1323 may be adapted to consume less power than the main processor 1321, or execute a particular function. The auxiliary processor 1323 may be implemented as being separate from, or a part of, the main processor 1321.

The auxiliary processor 1323 may control at least some of the functions or states related to at least one component (e.g., the display device 1360, the sensor module 1376, or the communication module 1390) among the components of the electronic device 1301, instead of the main processor 1321 while the main processor 1321 is in an inactive (e.g., sleep) state, or together with the main processor 1321 while the main processor 1321 is in an active state (e.g., executing an application). According to one embodiment, the auxiliary processor 1323 (e.g., an image signal processor or a communication processor) may be implemented as part of another component (e.g., the camera module 1380 or the communication module 1390) functionally related to the auxiliary processor 1323.

The memory 1330 may store various data used by at least one component (e.g., the processor 1320 or the sensor module 1376) of the electronic device 1301. The various data may include, for example, software (e.g., the program 1340) and input data or output data for a command related thereto. The memory 1330 may include the volatile memory 1332 or the non-volatile memory 1334.

The program 1340 may be stored in the memory 1330 as software, and may include, for example, an operating system (OS) 1342, middleware 1344, or an application 1346.

The input device 1350 may receive a command or data to be used by other components (e.g., the processor 1320) of the electronic device 1301, from the outside (e.g., a user) of the electronic device 1301. The input device 1350 may include, for example, a microphone, a mouse, or a keyboard.

The sound output device 1355 may output sound signals to the outside of the electronic device 1301. The sound output device 1355 may include, for example, a speaker or a receiver. The speaker may be used for general purposes, such as playing multimedia or recording, and the receiver may be used for receiving an incoming call. According to one embodiment, the receiver may be implemented as being separate from, or a part of, the speaker.

The display device 1360 may visually provide information to the outside (e.g., a user) of the electronic device 1301. The display device 1360 may include, for example, a display, a hologram device, or a projector and control circuitry to control a corresponding one of the display, hologram device, and projector. According to one embodiment, the display device 1360 may include touch circuitry adapted to detect a touch, or sensor circuitry (e.g., a pressure sensor) adapted to measure the intensity of force incurred by the touch.

The audio module 1370 may convert a sound into an electrical signal and vice versa. According to one embodiment, the audio module 1370 may obtain the sound via the input device 1350, or output the sound via the sound output device 1355 or a headphone of an external electronic device 1302 directly (e.g., wiredly) or wirelessly coupled with the electronic device 1301.

The sensor module 1376 may detect an operational state (e.g., power or temperature) of the electronic device 1301 or an environmental state (e.g., a state of a user) external to the electronic device 1301, and then generate an electrical signal or data value corresponding to the detected state. The sensor module 1376 may include, for example, a gesture sensor, a gyro sensor, an atmospheric pressure sensor, a magnetic sensor, an acceleration sensor, a grip sensor, a proximity sensor, a color sensor, an infrared ($I_R$) sensor, a biometric sensor, a temperature sensor, a humidity sensor, or an illuminance sensor.

The interface 1377 may support one or more specified protocols to be used for the electronic device 1301 to be coupled with the external electronic device 1302 directly (e.g., wiredly) or wirelessly. According to one embodiment, the interface 1377 may include, for example, a high definition multimedia interface (HDMI), a universal serial bus (USB) interface, a secure digital (SD) card interface, or an audio interface.

A connecting terminal 1378 may include a connector via which the electronic device 1301 may be physically connected with the external electronic device 1302. According to one embodiment, the connecting terminal 1378 may include, for example, an HDMI connector, a USB connector, an SD card connector, or an audio connector (e.g., a headphone connector).

The haptic module 1379 may convert an electrical signal into a mechanical stimulus (e.g., a vibration or a movement) or an electrical stimulus which may be recognized by a user via tactile sensation or kinesthetic sensation. According to one embodiment, the haptic module 1379 may include, for example, a motor, a piezoelectric element, or an electrical stimulator.

The camera module 1380 may capture a still image or moving images. According to one embodiment, the camera module 1380 may include one or more lenses, image sensors, image signal processors, or flashes.

The power management module 1388 may manage power supplied to the electronic device 1301. The power management module 1388 may be implemented as at least part of, for example, a power management integrated circuit (PMIC).

The battery 1389 may supply power to at least one component of the electronic device 1301. According to one embodiment, the battery 1389 may include, for example, a primary cell which is not rechargeable, a secondary cell which is rechargeable, or a fuel cell.

The communication module 1390 may support establishing a direct (e.g., wired) communication channel or a wireless communication channel between the electronic device 1301 and the external electronic device (e.g., the electronic device 1302, the electronic device 1304, or the server 1308) and performing communication via the established communication channel. The communication module 1390 may include one or more communication processors that are operable independently from the processor 1320 (e.g., the application processor) and supports a direct (e.g., wired) communication or a wireless communication. According to one embodiment, the communication module 1390 may include a wireless communication module 1392 (e.g., a cellular communication module, a short-range wireless communication module, or a global navigation satellite system (GNSS) communication module) or a wired communication module 1394 (e.g., a local area network (LAN) communication module or a power line communication (PLC) module). A corresponding one of these communication modules may communicate with the external electronic device via the first network 1398 (e.g., a short-range communication network, such as Bluetooth™, wireless-fidelity (Wi-Fi) direct, or a standard of the Infrared Data Association (IrDA)) or the second network 1399 (e.g., a long-range communication network, such as a cellular network, the Internet, or a computer network (e.g., LAN or wide area network (WAN)). These various types of communication modules may be implemented as a single component (e.g., a single IC), or may be implemented as multiple components (e.g., multiple ICs) that are separate from each other. The wireless communication module 1392 may identify and authenticate the electronic device 1301 in a communication network, such as the first network 1398 or the second network 1399, using subscriber information (e.g., international mobile subscriber identity (IMSI)) stored in the subscriber identification module 1396.

The antenna module 1397 may transmit or receive a signal or power to or from the outside (e.g., the external electronic device) of the electronic device 1301. According to one embodiment, the antenna module 1397 may include one or more antennas, and, therefrom, at least one antenna appropriate for a communication scheme used in the communication network, such as the first network 1398 or the second network 1399, may be selected, for example, by the communication module 1390 (e.g., the wireless communication module 1392). The signal or the power may then be transmitted or received between the communication module 1390 and the external electronic device via the selected at least one antenna.

At least some of the above-described components may be mutually coupled and communicate signals (e.g., commands or data) therebetween via an inter-peripheral communication scheme (e.g., a bus, a general purpose input and output (GPIO), a serial peripheral interface (SPI), or a mobile industry processor interface (MIPI)).

According to one embodiment, commands or data may be transmitted or received between the electronic device 1301 and the external electronic device 1304 via the server 1308 coupled with the second network 1399. Each of the electronic devices 1302 and 1304 may be a device of a same type as, or a different type, from the electronic device 1301. All or some of operations to be executed at the electronic device 1301 may be executed at one or more of the external electronic devices 1302, 1304, or 1308. For example, if the electronic device 1301 should perform a function or a service automatically, or in response to a request from a user or another device, the electronic device 1301, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1301. The electronic device 1301 may provide the outcome, with or without further processing of the outcome, as at least part of a reply to the request. To that end, a cloud computing, distributed computing, or client-server computing technology may be used, for example.

One embodiment may be implemented as software (e.g., the program 1340) including one or more instructions that are stored in a storage medium (e.g., internal memory 1336 or external memory 1338) that is readable by a machine (e.g., the electronic device 1301). For example, a processor of the electronic device 1301 may invoke at least one of the one or more instructions stored in the storage medium, and execute it, with or without using one or more other components under the control of the processor. Thus, a machine may be operated to perform at least one function according to the at least one instruction invoked. The one or more instructions may include code generated by a complier or code executable by an interpreter. A machine-readable storage medium may be provided in the form of a non-transitory storage medium. The term "non-transitory" indicates that the storage medium is a tangible device, and does not include a signal (e.g., an electromagnetic wave), but this term does not differentiate between where data is semi-permanently stored in the storage medium and where the data is temporarily stored in the storage medium.

According to one embodiment, a method of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., Play Store™), or between two user devices (e.g., smart phones)

directly. If distributed online, at least part of the computer program product may be temporarily generated or at least temporarily stored in the machine-readable storage medium, such as memory of the manufacturer's server, a server of the application store, or a relay server.

According to one embodiment, each component (e.g., a module or a program) of the above-described components may include a single entity or multiple entities. One or more of the above-described components may be omitted, or one or more other components may be added. Alternatively or additionally, a plurality of components (e.g., modules or programs) may be integrated into a single component. In this case, the integrated component may still perform one or more functions of each of the plurality of components in the same or similar manner as they are performed by a corresponding one of the plurality of components before the integration. Operations performed by the module, the program, or another component may be carried out sequentially, in parallel, repeatedly, or heuristically, or one or more of the operations may be executed in a different order or omitted, or one or more other operations may be added.

Although certain embodiments of the present disclosure have been described in the detailed description of the present disclosure, the present disclosure may be modified in various forms without departing from the scope of the present disclosure. Thus, the scope of the present disclosure shall not be determined merely based on the described embodiments, but rather determined based on the accompanying claims and equivalents thereto.

What is claimed is:

1. A method for biosignal detection and analysis, the method comprising:
   emitting, from a light source positioned on a substrate, an electromagnetic spectral emission, including polarized light, that is reflected on a surface,
   collecting attributes from the reflected electromagnetic spectral emission by at least one pixel positioned on the substrate,
   calculating Stokes parameters based on the collected attributes,
   obtaining a parameter representing a diattenuation based on the Stokes parameters, the parameter indicating one or more ratios of intensities of different polarization states,
   determining, based on the parameter representing the diattenuation, at least one time-varying biosignal, wherein a first amplitude of the parameter representing the diattenuation is determined based on a first time point and a second amplitude of the parameter representing the diattenuation is determined based on a second time point after the first time point, and
   analyzing the at least one time-varying biosignal to estimate health-related information,
   wherein the collected attributes comprise at least one of a light intensity of a predetermined polarization state, a light intensity for a wavelength range, or a light intensity for multiple pixels.

2. The method of claim 1, wherein the surface on which the electromagnetic spectral emission is reflected is a living tissue.

3. The method of claim 1, wherein the electromagnetic spectral emission is at least one of a collimated emission, a diffused emission, a polarized emission, a multispectral emission, a pulsed emission, a continuous emission, a visible spectrum emission or an infrared emission.

4. The method of claim 1, wherein the at least one pixel detects a wavelength range and at least one polarization state.

5. The method of claim 4, wherein the at least one pixel comprises hardware filters configured to allow the wavelength range and the at least one polarization state to pass through while restricting other wavelength ranges and polarization states to pass through.

6. The method of claim 1, wherein the attributes collected from the reflected electromagnetic spectral emission comprise at least one of a spectrum, a polarization state, a light intensity, or a depth.

7. The method of claim 1, wherein calculating the Stokes parameters is performed for at least one pixel using intensity data of the at least one pixel using a polarization state and wavelength range filter.

8. The method of claim 1, wherein the at least one time-varying biosignal is determined based on at least one of spectral changes or a depth estimation.

9. The method of claim 1, wherein the at least one time-varying biosignal is analyzed to estimate the health-related information by processing the reflected electromagnetic spectral emission with a polarized emission.

10. The method of claim 1, wherein the polarized light is comprised of at least one of linear polarization, circular polarization, or elliptical polarization.

11. The method of claim 1, wherein the health-related information includes at least one of heart-rate information, respiratory rate information, hypertension signatures, red blood cell concentration information, blood saturation information, a continuous blood pressure, pulse rate information, a pulse pressure, cardiovascular conditions, stroke volume information, cardiac output information, a one lead electrocardiogram (ECG), a systematic vascular resistance, a cardiac index, a mean arterial pressure, antioxidants, melanoma information, triglyceride information, cholesterol information, or beta carotene information.

12. A system for biosignal detection and analysis, the system comprising:

a light source positioned on a substrate and configured to emit an electromagnetic spectral emission, including polarized light, reflected on a surface;

a detector configured to collect attributes of the reflected electromagnetic spectral emission by at least one pixel positioned on the substrate; and a processor configured to:

calculate Stokes parameters based on the collected attributes, obtain a parameter representing a diattenuation based on the Stokes parameters, the parameter indicating one or more ratios of intensities of different polarization states, determine, based on the parameter representing the diattenuation, at least one time-varying biosignal, wherein a first amplitude of the parameter representing the diattenuation is determined based on a first time point and a second amplitude of the parameter representing the diattenuation is determined based on a second time point after the first time point, and analyze the at least one time-varying biosignal to estimate health-related information, wherein the collected attributes comprise at least one of a light intensity of a predetermined polarization state, a light intensity for a wavelength range, or a light intensity for multiple pixels.

13. The system of claim 12, wherein the at least one time-varying biosignal is determined based on at least one of spectral changes or a depth estimation.

14. The system of claim 12, wherein the polarized light is comprised of at least one of linear polarization, circular polarization, or elliptical polarization.

15. The system of claim 12, wherein the health-related information includes at least one of heart-rate information, respiratory rate information, hypertension signatures, red blood cell concentration information, blood saturation information, a continuous blood pressure, pulse rate information, a pulse pressure, cardiovascular conditions, stroke volume information, cardiac output information, a one lead electrocardiogram (ECG), a systematic vascular resistance, a cardiac index, a mean arterial pressure, antioxidants, melanoma information, triglyceride information, cholesterol information, or beta carotene information.

16. A method for biosignal detection and analysis, the method comprising:

emitting, from a light source positioned on a substrate, polarized light that is reflected on a surface, detecting the reflected polarized light using a pixel positioned on the substrate having four polarizing filters, calculating Stokes parameters based on attributes of the polarized light identified using the four polarizing filters, obtaining a parameter representing a diattenuation based on the Stokes parameters, the parameter indicating one or more ratios of intensities of different polarization states, determining, based on the parameter representing the diattenuation, at least one time-varying biosignal, wherein a first amplitude of the parameter representing the diattenuation is determined based on a first time point and a second amplitude of the parameter representing the diattenuation is determined based on a second time point after the first time point, and analyzing the at least one time-varying biosignal to estimate health-related information, wherein the attributes comprise at least one of a light intensity of a predetermined polarization state, a light intensity for a wavelength range, or a light intensity for multiple pixels.

17. The method of claim 16, wherein the at least one time-varying biosignal is determined based on at least one of spectral changes or a depth estimation.

18. The method of claim 16, wherein the polarized light is comprised of at least one of linear polarization, circular polarization, or elliptical polarization.

19. The method of claim 16, wherein the health-related information includes at least one of heart-rate information, respiratory rate information, hypertension signatures, red blood cell concentration information, blood saturation information, a continuous blood pressure, pulse rate information, a pulse pressure, cardiovascular conditions, stroke volume information, cardiac output information, a one lead electrocardiogram (ECG), a systematic vascular resistance, a cardiac index, a mean arterial pressure, antioxidants, melanoma information, triglyceride information, cholesterol information, or beta carotene information.

* * * * *